(12) United States Patent
Davis et al.

(10) Patent No.: US 9,255,120 B2
(45) Date of Patent: Feb. 9, 2016

(54) CONVERSION OF GLUCOSE TO SORBOSE

(71) Applicant: CALIFORNIA INSTITUTE OF TECHNOLOGY, Pasadena, CA (US)

(72) Inventors: Mark E. Davis, Pasadena, CA (US); Rajamani Gounder, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/197,511

(22) Filed: Mar. 5, 2014

(65) Prior Publication Data

US 2014/0309415 A1 Oct. 16, 2014

Related U.S. Application Data

(60) Provisional application No. 61/811,010, filed on Apr. 11, 2013.

(51) Int. Cl.
*C07B 37/08* (2006.01)
*C07H 3/02* (2006.01)
*C07D 307/62* (2006.01)

(52) U.S. Cl.
CPC ............... *C07H 3/02* (2013.01); *C07D 307/62* (2013.01)

(58) Field of Classification Search
None
See application file for complete search history.

(56) References Cited

U.S. PATENT DOCUMENTS

| 2,189,778 | A | 2/1940 | Otto |
| 4,373,025 | A | 2/1983 | Neuzil et al. |
| 4,410,501 | A | 10/1983 | Taramasso et al. |
| 6,284,499 | B1 | 9/2001 | Kishimoto et al. |
| 7,572,925 | B2 | 8/2009 | Dumesic et al. |
| 2002/0076771 | A1 | 6/2002 | Kumar |
| 2004/0121437 | A1 | 6/2004 | Scheels |
| 2005/0201920 | A1 | 9/2005 | Shan et al. |
| 2010/0121096 | A1 | 5/2010 | Taarning et al. |
| 2011/0207923 | A1 | 8/2011 | Moliner-Marin et al. |

FOREIGN PATENT DOCUMENTS

| EP | 0176621 | 4/1986 |
| EP | 0302970 | 2/1989 |
| JP | S64-50893 | 2/1989 |
| JP | 2001-114511 | 4/2001 |
| JP | 2009-201405 | 9/2009 |
| WO | WO 96-17837 | 6/1996 |
| WO | WO 2006/134374 A2 | 12/2006 |
| WO | WO 2007/146636 A1 | 12/2007 |
| WO | WO 2012-050625 | 4/2012 |

OTHER PUBLICATIONS

Andy and David, "Dehydrogenation of Propane Over Platinum Containing CIT-6", Ind. Eng. Chem. Res., Jun. 2004, 43(12), 2922-2928.
Baerlocher et al., "Atlas of Zeolite Framework Types", Fourth Edition, 1996, 62-63.
Bermejo-Deval et al., "Framework And Extraframework Tin Sites in Zeolite Beta React Glucose Differently", ACS Catalysis, Oct. 23, 2012, 9 pages.
Blasco et al., "Synthesis, Characterization, Catalytic Activity of Ti-MCM-41 Structures", J. Catal., Sep. 1995, 156(1), 65-74.
Corma et al., "Al-Free Sn-Beta Zeolite as a Catalyst for the Selective Reduction of Carbonyl Compounds (Meerwein-Ponndorf-Verley Reaction)", J. Am. Chem. Soc, Apr. 3, 2002, 124(13), 3194-3195.
Corma et al., "Lewis Acidic Sn(IV) Centers—Grafted Onto MCM-41—as Catalytic Sites for the Baeyer-Villiger Oxidation With Hydrogen Peroxide", Journal of Catalysis., Oct. 2003, 219(1), 242-246.
Corma et al., "Mesoporous Molecular Sieve Sn-MCM-41 as Baeyer-Villiger Oxidation Catalyst for Sterically Demanding Aromatic and a,13-unsaturated Aldehydes", Arkivoc, Mar. 2005, 124-132.
Corma et al., "Sn-Zeolite Beta as a Heterogeneous Chemoselective Catalyst for Baeyer-Villiger Oxidations", Nature, Jul. 26, 2001, 412(6845), 423-425.
Corma et al., "Water Resistant, Catalytically Active Nb and Ta Isolated Lewis Acid Sites, Homogeneously Distributed by Direct Synthesis in a Beta Zeolite", J. Phys. Chem. C., Jun. 2009, 113(26), 11306-11315.
Corma et al., "Lewis acids: From conventional homogeneous to green homogenous and heterogeneous catalysis", Chem. Rev., 2003, 103(11), 4307-4365.
Hayashi and Sasaki, "Tin-Catalyzed Conversion of Trioses to Alkyl Lactates in Alcohol Solution", Chem. Commun., Apr. 2005, 21,2716-2718.
Holm et al., "Conversion of Sugars to Lactic Acid Derivatives Using Heterogeneous Zeotype Catalysts", Apr. 30, 2010, 328, 602-605.
International Patent Application No. PCT/US2011/021301: Written opinion dated May 30, 2012, 4 pages.
Khouw et al., "Synthesis and Physicochemical Properties of Zeolites Containing Framework Titanium", Micropor. Mater, 2, Jan. 1994, 425-437.
Lee et al, "Effective Gene Silencing by Multilayered siRNA-Coated Gold Nanoparticles", Small, 2011, 7, 3, 364-370.
Lytton-Jean et al., "Five Years of siRNA Delivery: Spotlight on Gold Nanoparticles", Small, 2011,7, 14, 1932-1937.
Roman-Leshkov et al., "Mechanism of Glucose Isomerization Using a Solid Lewis Acid Catalyst in Water", Angew. Chem. Inti, ed., Oct. 2010, 49, 8954-8957.
Roman-Leshkov et al., "Supporting Information—Supplementary Material", Angewandte Chemie, Nov. 2010, 8 pages.

(Continued)

*Primary Examiner* — Layla Bland
(74) *Attorney, Agent, or Firm* — Baker & Hostetler LLP

(57) ABSTRACT

The present invention is directed to methods for preparing sorbose from glucose, said method comprising: (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose. The sorbose may be (b) separated or isolated; or (c) converted to ascorbic acid.

40 Claims, 10 Drawing Sheets

(56) References Cited

OTHER PUBLICATIONS

Taarning et al., "Zeolite-Catalyzed Isomerization of Triose Sugars", Chem. Sus. Chem, Jun. 2009, 2(7), 625-627.
Tewari, "Supplementary Information—Thermodynamic Data", Applied Biochemistry and Biotechnology, Dec. 1990, 23(3), 187-203.
Angyal, Stephen, "The Lobry de Bruyn-Alberda van Ekenstein Transformation and Related Reactions", Glycoscience, Topics in Current Chemistry, 2001, 215, 1-14.
Bermejo-Deval, "Framework and Extraframework Tin Sites in Zeolite Beta React 2 Glucose Differently", ACS Catalysis, 2012, 2, 2705-2713.
Blasco et al, "Direct Synthesis and Characterization of Hydrophobic Aluminum-Free Ti-Beta Zeolite", J. Phys. Chem. B, 1998, 102 (1), pp. 75-88.
Corma et al. ARKIVOC 2007 (viii) 40-48.
Davis et al., "Aqueos-Phase Monosaccharide and Disaccharide Isomerization and Epimerization over Lewis Acid Sites in Hydrophobic Molecular Sieves", Elseveir Editorial System for Journal of Catalysis, 2013, 102 pages.
El Khadem et al, "Contribution of the Reaction Pathways Involved in the Isomerization of Monosaccharides by Alkali", Carbohydrate Research, 169, Nov. 15, 1987, 13-21.
Gounder, R., and Davis, M., "Beyond Shape Selective Catalysis With Zeolites: Hydrophobic Void Spaces in Zeolites Enable Catalysis in Liquid Water", Sep. 2013, 59(9), 3349-3358.
Granström et al, "Izumoring: A Novel and Complete Strategy for Bioproduction of Rare Sugars", Journal of Bioscience and Bioengineering, 2004, 97(2), 89-94.
Hanmoungjai et al, "L-Sorbose Production by Acidotolerant Acetic Acid Bacteria Isolated From Thailand Sources", Chiang Mai J. Sci., 2008, 35(2), 382-390.
Lima et al. "Isomerization of O-Glucose to D-Fructose Over Metallosilicate Solid Bases", Applied Catalysis, A: General 339 (2008) 21-27.
Moliner et al., "Tin-Containing Zeolites are Highly Active Catalysts for the Isomerixation of glucose in Water", PNAS, 107(14), Apr. 6, 2010, 6164-6168.
PTC tips, PTO Reaction of the Month, http://www.phasetransfer.com/03tip9.htm, 2003.
Que, L., and Gray, GR., "13C Nuclear Magnetic Resonance Spectra and the Tautomeric Equilibria of Ketohexoses in Solution", Biochemistry, Jan. 1, 1974, 13(1), 146-153.
Sowden, RG., and Thompson,RR., "The Isomerixation of D-glucose-1-$C^{14}$ to D- and L-sorbose-$C^{14}$ by a Strong Base Resin[1]", J. Am. Chem. Soc., Mar. 1958, 80(6), 1435-1437.
Angyal SJ, "The Lobry de Bruyn-Alberda van Ekenstein Transformation and Related Reactions", Topics in Current Chemistry, Mar. 2001, 215, p. 1-14.
Bílik et al., "Reactions of Saccharides Catalyzed by Molybdate Ions. XV. Mechanism of the Epimerization Reaction", Chem. zvesti, 1975, 29(5), 690-696.
Bílik et al., "Reactions of Saccharides Catalyzed by Molybdate Ions. XIX. Molybdate Complexes and Epimerization of Aldoses as a Function of pH", Chem. Zvesti, 1978, 32(2), 242-251.
Blair et al., "The Isomerization of D-Glucose to D- and L-Sorbose by a Strong Base Resin", J. Am. Chem. Soc, 1955, 77, 3323-3325.
Boronat et al., "Mechanism of the Meerwein-Ponndorft-Verley-Oppenauer (MPVO) Redox Equilibrium on Sn- and Zr-Beta Zeolite Catalysts", J. Phys. Chem. B, 2006, 110(42), 21168-21174, Published online: Sep. 22, 2006.
Boudrant, "Microbial Process for Ascorbic Acid Biosynthesis: A Review", Enzyme and Microbial Technology, May 1990, 12(5), 322-329.
Bremus et al., "The Use of Microorganisms in L-Ascorbic Acid Production", Journal of Biotechnology, Jun. 2006, 124(1), 196-205.
Collyer et al., "Observations of Reaction Intermediates and the Mechanism of Aldose-Ketose Interconversion by D-Xylose Isomerase", Proc. Natl. Acad. Sci. USA, 1990, 87(4), 1362-1366.
Corma et al., "Water-Resistant Solid Lewis Acid Catalysts: Meerwein-Ponndorf-Verley and Oppenauer Reactions Catalyzed by Tin-beta Zeolite", J. Catalysis, 2003, 215(2), 294-304.
Crueger et al., Glucose Transforming Enzymes. In Microbial Enzymes and Biotechnology, Fogarty, W.M; Kelly, C.T., Eds., Springer Netherlands: Netherlands, 1990, pp. 117-226.
de Bruyn et al., "Transformation reciproque des uns dans les autres des sucres gluconse, fructos et mannose", Recl. Trav. Chim. Pays.-Bas, 1895, 14, 203—Not in English(See cite No. 53).
DeWit et al., "Enolisation and Isomerisation of Monosaccharides in Aqueous, Alkaline Solution", Carbohydrate Research, 1979, 74(1), 157-175.
Eggersdorfer et al., "One Hundred Years of Vitamins—A Success Story of the Natural Sciences", Angewandte Chemie—Intl. Ed., 2012, 51(52), 12960-12990.
Fischer, "Mittheilungen", Ber. Dtsch. Chem. Ges., 1890, 23, 2114— Not in English (See cite No. 53).
Gunther et al., "Sn-Beta Zeolites with Borate Salts Catalyse the Epimerization of Carbohydrates Via an Interamolecular Carbon Shift", Nature Communications, 2012, 3(1109), 1-8.
Hancock et al., "Biotechnological Approaches for L-ascorbic Acid Production", Trends in Biotechnology, Jul. 1, 2002, 20(7), 299-305.
Kooyman et al., "The Isomerization of D-Glucose into D-Fuctose in Acqueous Alkaline Solutions", Carbohydrate Research, Mar. 1997, 54(1), 33-44.
Kovalesky et al., "Metal Ion Roles and the Movement of Hydrogen during Reaction Catalyzed by D-Xylose Isomerase: A Joint X-Ray and Neutron Diffraction Study)", Structure, Jun. 9, 2010, 18(6), 688-699.
Lobo, "Synthetic Glycolysis", ChemSusChem, Nov. 22, 2010, 3(11), 1237-1240.
Neuhaus et al., "The Nuclear Overhouser Effect in Structural and Conformational Analysis", VCH: Weinheim, 1989, 8 pages.
Osanai, "Nickle(II)-Catalyzed Rearrangements of Free Sugars", Top. Curr. Chem., 2001, 215, 43-76.
Román-Leshkov et al., "Activation of Carbonyl-containing Molecules with Solid Lewis Acids in Aqueous Media", ACS Catal., Sep. 28, 2011, 1, 1566-1580.
Speck, "The Lobry De Bruyn-Alberda Van Ekenstein Transformation", Advances in Carbohydrate Chemistry, 1958, 13, 63-103.
Yang et al., "Alkaline Degration of Glucose: Effect of Intial Concentration of Reactants", Carbohydrate Research, Jan. 4, 1996, 280(1), 27-45.
Japanese Patent Application No. 2012-549112: Notification of Reasons for Refusal dated Nov. 25, 2014, 11 pages with English Translation.
Miyazawa et al, "Hydrothermal Degradation of Polysaccharides in a Semi-Batch Reactor: Product Distribution as a Function of Severity Parameter", J. Mater. Sci., 2008, 43, 2447-2451, Published Online: Oct. 4, 2007.

FIG. 1A Lewis acid-mediated isomerization (intramolecular hydride shift)
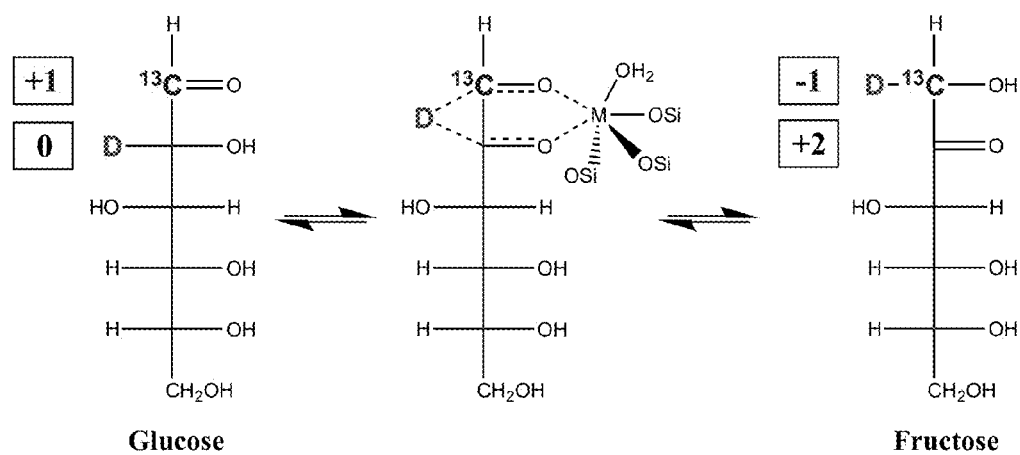
FIG. 1B Lewis acid-mediated epimerization (intramolecular carbon shift)
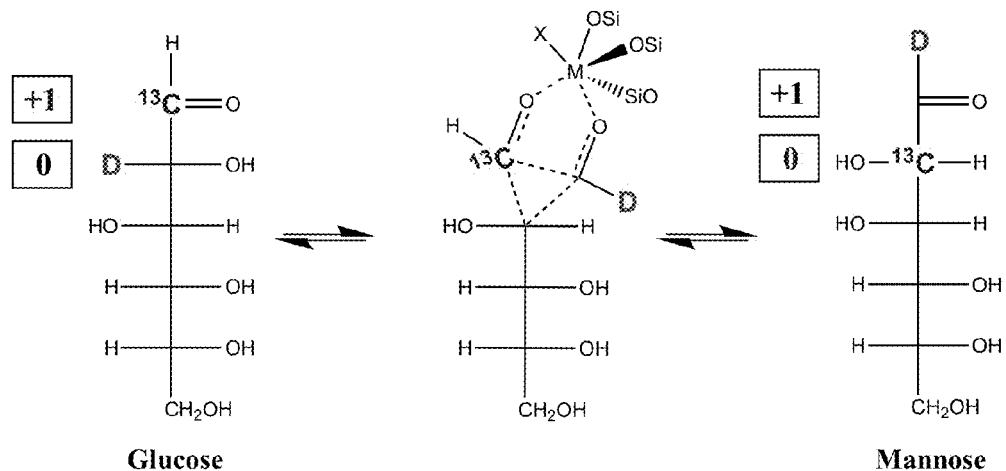

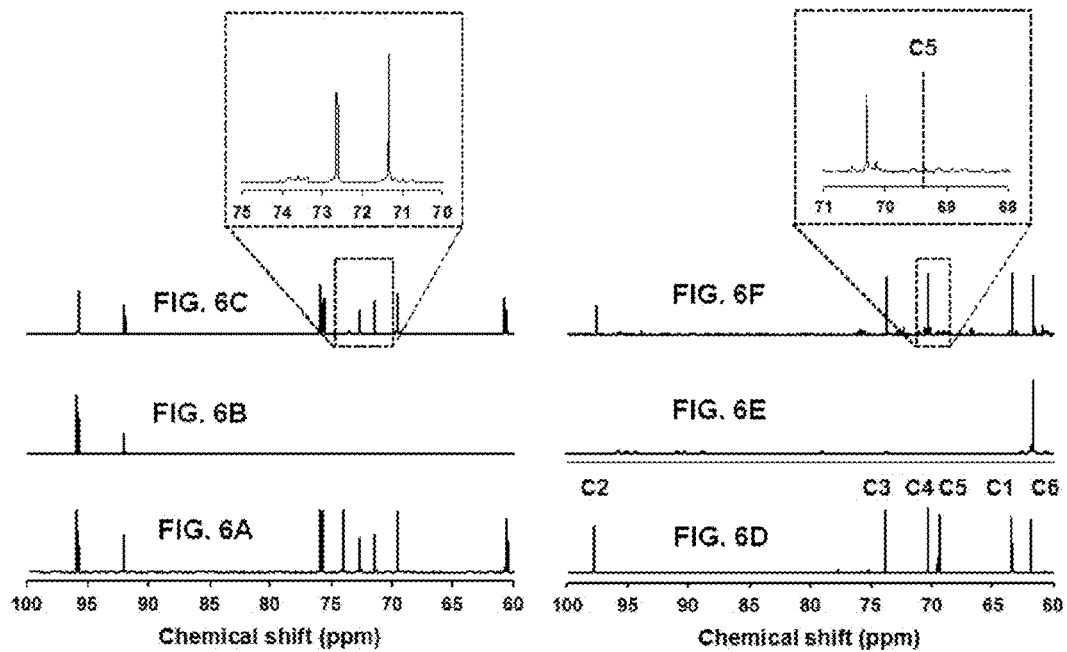
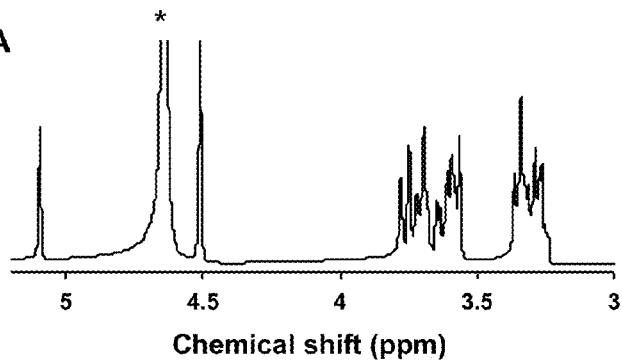
FIG. 7A
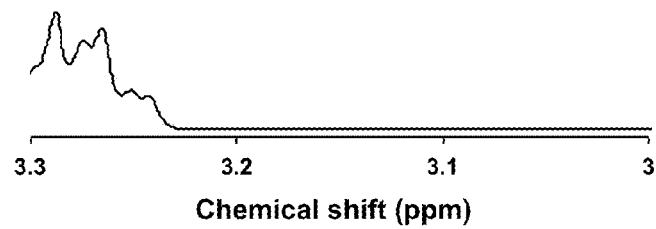
FIG. 7B

CONVERSION OF GLUCOSE TO SORBOSE

CROSS REFERENCE TO RELATED APPLICATIONS

This application claims the benefit of U.S. Patent Application Ser. No. 61/811,010, filed Apr. 11, 2013, which is incorporated by reference in its entirety.

GOVERNMENT RIGHTS

The subject matter disclosed herein was made with government support under grant number DE-SC0001004/T-106028 awarded by the Department of Energy. The Government has certain rights in the herein disclosed subject matter.

TECHNICAL FIELD

The disclosed invention is in the field of glucose isomerization.

BACKGROUND

D-glucose is used as a feedstock in the Reichstein synthesis of L-ascorbic acid (a form of vitamin C; ~$10^5$ tons produced annually worldwide) via L-sorbose intermediates. The conversion of D-glucose to L-sorbose currently requires the sequential hydrogenation of D-glucose to D-sorbitol over a nickel-based catalyst and selective oxidation of C2-OH groups in D-sorbitol to L-sorbose using microbiological enzymes. The production of sorbose, among a mixture of several aldohexose and ketohexose isomers, has been observed during reactions of glucose in alkaline media via 3,4-enediol intermediates, and via retro-aldol condensation to glyceraldehyde, isomerization to dihydroxyacetone, and realdolization of these triose intermediates. Heterogeneous base resins (Amberlite XE-48, Amberlite IRA-400) also convert D-(+)-glucose to a mixture of D-(+)-sorbose (~68%) and L-(−)-sorbose (~32%), among several other hexose products, via 3,4-enediol intermediates.

Glucose isomerization and epimerization reactions catalyzed by bases are known to proceed via abstraction of α-carbonyl protons to form 1,2-enediol intermediates, which undergo proton-transfer mediated rearrangements to form fructose and mannose (Lobry de Bruyn-Alberda van Ekenstein rearrangements; LdB-AvE). Double-bond isomerization of 1,2-enediols leads to a mixture of 2,3- and 3,4-enediol intermediates that are precursors to psicose, tagatose and sorbose ketohexoses (the C-3, C-4 and C-5 epimers of fructose, respectively) and other aldohexoses. As a result, selectivities to fructose, the preferred product of glucose conversion in alkaline media, decrease with increasing glucose conversion because of sequential 1,2-enediol rearrangements and because monosaccharides undergo retro-aldol condensation and other degradation pathways.

In contrast to base catalysts that initiate glucose isomerization via α-carbonyl abstraction, Lewis acids coordinate with and polarize oxygen atoms (O1) at glucose aldehyde carbons (C1) to enable nucleophilic addition preferentially at electron-deficient C-1 centers over other carbon atoms along the sugar backbone. (FIG. 1A) The ability of a single Lewis acid center to coordinate with glucose via a second oxygen atom located in another hydroxyl group along the sugar backbone, in turn, facilitates intramolecular skeletal rearrangements via migration of nucleophilic moieties to glucose C1 centers. Infrared (IR) and solid-state $^{13}C$ nuclear magnetic resonance (NMR) studies, together with quantum chemical calculations, have shown that Lewis acidic framework Sn centers isolated within zeolite beta (Sn-Beta) mediate glucose ring-opening and coordination with glucose O1 and O2 atoms. In turn, glucose-fructose isomerization occurs via subsequent intramolecular hydride shift from the C2 to C1 carbon atoms on open glucose chains. This isomerization mechanism is analogous to that mediated by two divalent Lewis acid metal centers (e.g., $Mg^{2+}$ or $Mn^{2+}$) that are spatially positioned within hydrophobic pockets of metalloenzymes (e.g., D-xylose isomerase) to facilitate glucose binding via O1 and O2 atoms prior to glucose-fructose isomerization.

Sn-Beta can also mediate glucose-mannose epimerization in methanol solvent, and in water in the presence of borate salts, via a Lewis-acid intramolecular carbon rearrangement known as the Bilik reaction. In the glucose-mannose epimerization mechanism, C3 carbon centers bound to C2 atoms behave as nucleophiles and migrate (along with the rest of the covalently bound sugar backbone) to electrophilic C1 centers (FIG. 1B). The mechanisms for framework Sn-mediated glucose-mannose epimerization and glucose-fructose isomerization are similar because they first require bidentate glucose coordination to metal centers via O1 and O2 atoms; they differ, in part, because C3 centers or hydridic species bound to glucose C2 centers respectively act as the nucleophiles that attack electron-deficient C1 centers (FIG. 1B). These intramolecular hydride and carbon shifts occur within glucose only with Lewis acidic framework Sn-Beta and not with base sites on extra framework $SnO_2$ domains, reflecting the requirement of Lewis acid centers to mediate the redistribution of oxidation states between carbon atoms in organic substrates at transition states for intramolecular or intermolecular Meerwein-Ponndorf-Verley aldehyde and ketone reduction and Oppenauer alcohol oxidation (MPVO) reactions.

SUMMARY

Various embodiments of the present invention provide processes for preparing sorbose from glucose, each process comprising: (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose; and (b) separating the sorbose.

Other embodiments provide processes for preparing ascorbic acid, each process comprising: (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose; (b) optionally separating the sorbose; and (c) converting the sorbose to ascorbic acid.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, processes, devices, and systems disclosed. In addition, the drawings are not necessarily drawn to scale. In the drawings:

FIG. 1A-B illustrates schematically a mechanism of glucose isomerization (FIG. 1A) and glucose epimerization (FIG. 1B) mediated by Lewis acid (M) centers in silicate frameworks on Sn-Beta. Oxidation states of C1 and C2 carbon atoms are shown in reactant and product sugars (depicted using Fischer projections). Mechanistic evidence for both reactions has been previously established based on isotopic (D, $^{13}$C) tracer studies using labeled glucose reactants; proposed transition states for both pathways are also shown. As shown herein, glucose first must undergo ring-opening at M sites to give the acyclic form prior to isomerization or epimerization.

FIG. 6A-F are the $^{13}$C NMR spectra of unlabeled glucose (FIG. 6A) and of the glucose fractions isolated after reaction of glucose-$^{13}$C-C1 (FIG. 6B) and glucose-D2 (FIG. 6C) with Ti-Beta in water at 373 K for 6 h. $^{13}$C NMR spectra of unlabeled sorbose (FIG. 6D) together with assignments for each carbon position in α-L-sorbopyranose, and of the sorbose fractions isolated after reaction of glucose-$^{13}$C-C1 (FIG. 6E) and glucose-D2 (FIG. 6F) with Ti-Beta in water at 373 K for 6 h.

FIG. 7A-B is the $^{1}$H NMR spectrum of glucose fraction after reaction of glucose-D2 with Ti-Beta in water at 373 K for 6 h. FIG. 7A is the region δ: 3-5.2 ppm; * denotes $H_2O$. FIG. 7B is the region δ: 3-3.3 ppm.

DETAILED DESCRIPTION OF ILLUSTRATIVE EMBODIMENTS

Figure 2:
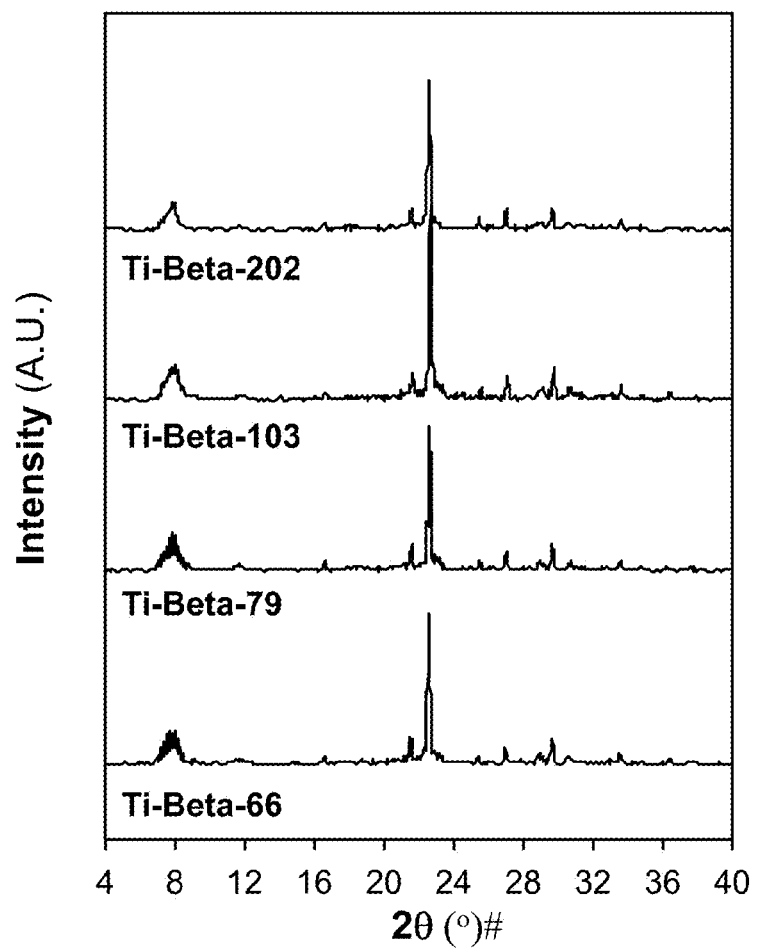
FIG. 2 are powder x-ray diffraction patterns of as-made Ti-Beta-66, Ti-Beta-79, Ti-Beta-107, Ti-Beta-202 (bottom to top) as described in Example 2.1. Suffix denotes Si/Ti ratio; all samples are consistent with the powder pattern for the beta topology.

The present invention is directed to processes for the catalytic conversion of glucose to sorbose and from glucose to ascorbic acid. The Examples described herein represent the first evidence for the direct isomerization of glucose to sorbose, a ketose sugar (the C5 epimer of fructose), which is mediated by Lewis acidic $Ti^{4+}$ centers incorporated into the framework of silica zeolite beta (Ti-Beta or Zr-Beta). The data and the mechanistic evidence presented herein, to the inventors' knowledge, constitute the first report of direct and stereospecific D-(+)-glucose to L-(−)-sorbose isomerization mediated by a Lewis acid center, or by any catalytic entity for that matter.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) is the facile operability of the methods (or the systems used in such methods or the compositions derived therefrom) to convert glucose, preferably D-(+)-glucose, to sorbose, preferably L-(−)-sorbose.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Various embodiments of the present invention provide methods or processes for preparing sorbose from glucose, each process comprising: (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose; and (b) separating the sorbose.

As used herein, the terms "methods" or "processes" may be used interchangeably.

In other embodiments, each process further embodiments further comprise converting the sorbose, whether generated in situ as in step (a) or as separated or isolated in step (b), to form ascorbic acid. That is, certain embodiments provide processes for preparing ascorbic acid, each process comprising: (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose; (b) optionally separating the sorbose; and (c) converting the sorbose to ascorbic acid.

It is appreciated that various types of silica-containing structures containing Lewis acidic $Ti^{4+}$ or $Zr^{4+}$ or both $Ti^{4+}$ and $Zr^{4+}$ framework centers may be applied individually or in combination with one another, either in a serial arrangement or temporal batchwise arangements, or both. It should also be appreciated that the conversion of the glucose to sorbose is catalytic with respect to the metal-silica-containing structures. See, e.g., Table 1.

In preferred embodiments, the silica-containing structure comprises or consists essentially of a zeolite having a topology of a 12 membered-ring or larger, provided the structures have Lewis acidic $Ti^{4+}$ or $Zr^{4+}$ or both $Ti^{4+}$ and $Zr^{4+}$ framework centers. In more embodiments, the zeolite has a *BEA topology. Such *BEA topological compositions may also be referred to as Ti-Beta or Zr-Beta compositions, according to nomenclature recognized by those skilled in the art. In such arrangements, the zeolite may comprise Lewis acidic $Ti^{4+}$ or $Zr^{4+}$ or both $Ti^{4+}$ and $Zr^{4+}$ framework centers, though it appears that those compositions containing Lewis acidic $Ti^{4+}$ framework centers are preferred. Without intending to be bound by the correctness of any particular theory, the topology of the zeolite having a 12 membered-ring (12-MR) or larger (which may alternatively described as providing pore sizes of 0.7 nanometers or above) is believed to be important so as to allow the reactants and products to migrate in and out of the structures, respectively. For example, 10 membered rings (10-MR) and smaller will likely be too small to adsorb glucose or accommodate the puckered C1-O5 hydride shift transition state for glucose-to-sorbose isomerization.

The processes are flexible in the Si/Ti (and/or Zr) atomic ratios that can be employed in the zeolite structures, and in some embodiment, the zeolite has a composition such that the atomic ratio of Si to Ti, Zr, or combination of Ti and Zr, is in a range of from about 35 to about 250. In certain other individual embodiments, the zeolite has a composition such that the atomic ratio of Si to Ti, Zr, or combination of Ti and Zr is in a range having a lower boundary of about 35, about 40, about 65, about 80, about 100, or about 120, and an upper boundary of 200, about 120, about 100, or about 80; for example in a range of from about 65 to about 120.

In other separate embodiments, the silica-containing structures comprise or consist essentially of an ordered or amorphous silica, again provided that the structure contains Lewis acidic $Ti^{4+}$ or $Zr^{4+}$ or both $Ti^{4+}$ and $Zr^{4+}$ framework centers. Non-limiting examples of ordered mesoporous silica material include MCM-41, MCM-48, and SBA-15 structures. Non-limiting examples of amorphous silica-containing titania or zirconia centers in amorphous silica include, for example $TiO_2$—$SiO_2$ or $ZrO_2$—$SiO_2$ co-precipitated or formed as a mixed oxide. In these ordered or amorphous structures, Each of these types of ordered or amorphous structures serve as appropriate templates for the catalytic activity of the $Ti^{4+}/Zr^{4+}$, though zeolites, though the selectivities to form sorbose are higher on zeolite materials, for example Ti-Beta, than on ordered mesoporous materials, like MCM-41. That is, the main differences among all of these three classes of materials is that the differences in selectivity for the glucose-to-sorbose transformation.

As stated above, independent embodiments of the inventive processes use silica-containing structures containing Lewis acidic $Ti^{4+}$ or $Zr^{4+}$ or both $Ti^{4+}$ and $Zr^{4+}$ framework centers. Those structures, especially beta zeolites containing Lewis acidic $Ti^{4+}$ framework centers are preferred.

As described above, the methods provide for the transformation of glucose to sorbose, and especially for the conversion of D-(+)-glucose to L-(−)-sorbose. As described elsewhere herein, this stereoselective transformation has important commercial implications, as L-(−)-sorbose is a useful intermediate in the productions of L-ascorbic acid. Accordingly, various embodiments, then, include those processes or methods encompassing the conversion of D-(+)-glucose to L-ascorbic acid using the inventive methods presented herein.

To this point, the processes have been described in terms of contacting glucose with the catalysts under reaction conditions sufficient to isomerize the glucose to sorbose. In some embodiments, the reactions are conducted in the presence of an aqueous liquid. As used herein, unless otherwise stated, the term "aqueous" refers to a liquid medium comprising at least about 98% by weight water, relative to the weight of the entire liquid medium (i.e., not including reactants). In other embodiments, if specifically stated as such, include those where the term "aqueous" refers to liquids comprising at least about 80%, at least about 85%, at least about 90%, at least about 95%, or substantially 100% water (again, not including reactants).

In other embodiments, the reactions are conducted in the presence of an alcoholic medium. As used herein, unless otherwise stated, the term "alcoholic medium" refers to a liquid medium that comprises at least about 98% by weight of an alcohol, relative to the weight of the entire liquid medium (i.e., not including reactants). If specifically stated as such, in other embodiments, the term "alcoholic medium" may refer to liquids comprising at least about 80%, at least about 85%, at least about 90%, at least about 95%, or substantially 100% of an alcohol, relative to the weight of the entire liquid (again, not including reactants). Certain embodiments provide for the use of short chain alcohols (e.g., methanol, ethanol, n-propanol, or isopropanol) for this purpose. The use of methanol appears to be preferred. As can be seen in Table 1, Example 3.1, the formation of sorbose runs in parallel with the formation of fructose, though the use of alcohol, especially methanol, favors the formation of the sorbose.

Note that the classification of aqueous and alcoholic liquids or solvents are subsets of those embodiments wherein the weight ratio of water to alcohol is about 5:95, 10:90, 20:80, 30:70, 40:60, 50:50, 60:40, 70:30, 80:20, 90:10, or 95:5, relative to the weight of the combined water and alcohol.

The processes are also flexible with respect to loadings of reactants and catalysts. While there does not appear to be a theoretical lower limit to the ratio of glucose to Ti (and/or Zr), in practice, embodiments include those where the molar ratio of glucose to the Ti, Zr, or combination of Ti and Zr is in a range of from about 5 to about 500. And while not necessarily constrained by these limits, in other embodiments, the glucose concentration in the aqueous solvent is in a range of from about 0.1 wt % to about 45 wt %, relative to the combined weight of the glucose and aqueous solvent. In those embodiments where an alcoholic solvent is used, a glucose concentration in a range of from about 0.1 wt % to about 2 wt %, relative to the combined weight of the glucose and alcoholic solvent appears to work well.

The processes are operable at relatively modest temperatures. In certain embodiments, the reaction conditions comprise heating the reaction mixture to at least one temperature in a range of from about 40° C. to about 200° C., the upper limit being the temperature at which the glucose degrades in the solvent. In other embodiments, the reaction conditions comprise heating the reaction mixture to at least one temperature in a range of from about 80° C. to about 120° C. or from about 100° C. to about 120° C. Given the volatility of the solvents employed in these processes, reactions may be (and are preferably) conducted in sealed reactors, such that local pressures are reflective of solvent boiling point. The reactions may be conducted aerobically or anaerobically. In the Examples cited herein, no attempt was made to exclude air from the reaction conditions.

In those embodiments where the sorbose is separated, this unit operation may comprise filtration, crystallization, freeze-thawing, chromatographic separation (i.e., employing a column capable of separating the sorbose from other reactants and products), solvent removal (e.g., using a centrifugal evaporator), or a combination thereof. The specific methods or processes depend on the reaction conditions employed (e.g., the levels of the glucose-sorbose in the reaction mixture relative to the amount of solvent), the specific nature of the catalyst, the desired purity, or a combination thereof. It would be well within the skill of the person of ordinary skill in the art to define the process most suitable for their desired product quality.

Further, the conversion of sorbose to ascorbic acid is well known, being commercially practiced by various processes in the latter stages of the so-called the Reichstein or Reichstein-Heyns process. Such latter stage processes include, for example, formation of 2-keto-L-gulonic acid by (a) acetal protection of ring hydroxyls followed by the chemical oxidation of the protected sorbose by hypochlorite or permanganate or (b) oxidation of the sorbose using oxygen and a noble metal catalyst, such as platinum (see, e.g., U.S. Pat. No. 2,189,778); followed by a gamma-lactonization of the formed intermediate, with removal of water. These steps may also be employed with the inventive processes described herein for the formation of the sorbose to provide embodiments directed to the conversion of glucose to ascorbic acid. Other methods or processes may also be used, such as those described by Granstrom, et al., *J. Biosci. Bioeng.*, 97 (2004) 89, which is incorporated by reference herein for its teaching of this conversion.

TERMS

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled in the relevant art. However, so as to avoid misunderstanding, the meanings of certain terms will be specifically defined or clarified.

"Optional" or "optionally" means that the subsequently described circumstance may or may not occur, so that the description includes instances where the circumstance occurs and instances where it does not. For example, the phrase "optionally separating the sorbose" means that a sorbose may or may not be separated from other materials in the method, and, thus, the description includes separate embodiments where the sorbose is separated and where the sorbose is not separated, such that subsequence steps are conducted on isolated or in situ generated sorbose.

The terms "separating" or "separated" carries their ordinary meaning as would be understood by the skilled artisan, insofar as it connotes separating or isolating the material (e.g., sorbose) from other starting materials or co-products or side-products (impurities) associated with the reaction conditions yielding the material. As such, it infers that the skilled artisan at least recognizes the existence of the product and takes specific action to separate or isolate it. Absolute purity is not required, though preferred, as the material may contain minor amounts of impurities and the separated or isolated material may contain residual solvent or be dissolved within a solvent used in the reaction or subsequent purification of the material.

The following listing of embodiments is intended to complement, rather than displace or supersede, the previous descriptions.

Embodiment 1

A process for preparing sorbose from glucose, said process comprising: (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose; and (b) separating the sorbose.

Embodiment 2

A process for preparing ascorbic acid, said process comprising: (a) contacting the glucose with a silica-containing structure comprising a zeolite having a topology of a 12 membered-ring or larger, an ordered mesoporous silica material (e.g., MCM-41, MCM-48, SBA-15), or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose; (b) optionally separating the sorbose; and (c) converting the sorbose to ascorbic acid.

Embodiment 3

The process of Embodiment 1 or 2, wherein the process comprises: (a) contacting the glucose with the silica zeolite containing the Lewis acidic $Ti^{4+}$ or $Zr^{4+}$ or both $Ti^{4+}$ and $Zr^{4+}$ framework centers under reaction conditions sufficient to isomerize the glucose to sorbose.

Embodiment 4

The process of any one of Embodiments 1 to 3, wherein the silica zeolite comprises a Ti-Beta zeolite or a Zr-Beta zeolite.

Embodiment 5

The process of Embodiment 1 or 2, wherein the process comprises: (a) contacting the glucose with the ordered mesoporous silica material (e.g., MCM-41, MCM-48, SBA-15) containing Lewis acidic $Ti^{4+}$ or $Zr^{4+}$ or both $Ti^{4+}$ and $Zr^{4+}$ framework centers under reaction conditions sufficient to isomerize the glucose to sorbose.

Embodiment 6

The process of Embodiment 1 or 2, wherein the process comprises: (a) contacting the glucose with the amorphous silica containing Lewis acidic $Ti^{4+}$ or $Zr^{4+}$ or both $Ti^{4+}$ and $Zr^{4+}$ framework centers under reaction conditions sufficient to isomerize the glucose to sorbose.

Embodiment 7

The process of any one of Embodiments 1 to 6, wherein the silica-containing structure contains Lewis acidic $Ti^{4+}$ framework centers.

Embodiment 8

The process of any one of Embodiments 1 to 7, wherein the sorbose is L-(−)-sorbose and the glucose is D-(+)-glucose.

Embodiment 9

The process of any one of Embodiments 2 to 8, wherein the ascorbic acid is L-ascorbic acid.

Embodiment 10

The process of any one of Embodiments 1 to 9, wherein the reaction conditions comprise contacting the glucose with the silica zeolite, ordered mesoporous silica material, or amorphous silica containing the Lewis acidic $Ti^{4+}$ or $Zr^{4+}$ or both $Ti^{4+}$ and $Zr^{4+}$ framework in the presence of an aqueous or an alcoholic liquid.

Embodiment 11

The process of any one of Embodiments 1 to 10, wherein the reaction conditions comprise contacting the glucose with the zeolite in the presence of an alcohol.

Embodiment 12

The process of Embodiment 10 or 11, wherein the alcohol is methanol.

Embodiment 13

The process of any one of Embodiments 1 to 4 or 6 to 12, wherein the zeolite has a composition such that the atomic ratio of Si to Ti, Zr, or combination of Ti and Zr is in a range of from about 35 to about 250.

Embodiment 14

The process of Embodiment 13, wherein the the zeolite has a composition such that the atomic ratio of Si to Ti, Zr, or combination of Ti and Zr is in a range of from about 65 to about 120.

Embodiment 15

The process of any one of Embodiments 1 to 14, wherein the molar ratio of glucose to Ti, Zr, or combination of Ti and Zr is in a range of from about 5 to about 500.

Embodiment 16

The process of any one of Embodiments 1 to 15, wherein the glucose concentration in aqueous solvent is in a range of from about 0.1 w/w to about 45 w/w, relative to the weight of the solvent.

Embodiment 17

The process of any one of Embodiments 1 to 16, wherein the glucose concentration in methanol solvent is in a range of from about 0.1 w/w to about 2 w/w, relative to the weight of the solvent.

Embodiment 18

The process of any one of Embodiment 1 to 17, wherein the reaction conditions comprise heating the reaction mixture to a temperature in a range of from about 60° C. to about 200° C., or from about 80° C. to about 120° C., or from about 100° C. to about 120° C.

Embodiment 19

The process of any one of Embodiments 1 to 18, wherein the sorbose is separated or isolated by filtration, crystallization, freeze-thawing, chromatographic separation (i.e., employing a column capable of separating the sorbose from other reactants and products), solvent removal (e.g., using a centrifugal evaporator), or a combination thereof.

Embodiment 20

The process of any one of Embodiments 2 to 19, comprising forming 2-keto-L-gulonic acid by (a) acetal protection of ring hydroxyls followed by the chemical oxidation of the protected sorbose by hypochlorite or permanganate or (b) oxidation of the sorbose using oxygen and a noble metal catalyst, such as platinum, or by both (a) and (b).

Embodiment 21

The process of Embodiment 20, further comprising employing conditions to ring close by gamma-lactonization of the 2-keto-L-gulonic acid, with removal of water

Embodiment 22

The process of any one of Embodiments 2 to 21, wherein converting the sorbose to ascorbic acid comprises a sequential oxidation step followed by a gamma lactonization with removal of water step, for example as practiced in the Reichstein process.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

Overview of Specific Experimental Results

Silica zeolite beta containing Lewis acidic framework $Ti^{4+}$ (Ti-Beta) has been shown to catalyze the isomerization of D-glucose to L-sorbose apparently (based on the information below) via intramolecular C5-C1 hydride shift steps. Glucose isomerization to sorbose occurred in parallel to isomerization to fructose on Ti-Beta in both water and methanol solvents. At 373 K, fructose was the predominant product in water, while sorbose was the predominant product in methanol. Isotopic tracer studies showed that $^{13}C$ and D labels placed respectively at the C1 and C2 positions of glucose were retained respectively at the C6 and C5 positions of sorbose, consistent with an intramolecular C5-C1 hydride shift. This direct Lewis acid-mediated pathway for glucose-sorbose isomerization appears to be unprecedented among heterogeneous or biological catalysts, and sharply contrasts indirect base-mediated glucose-sorbose isomerization that proceeds via 3,4-enediol intermediates or via retro-aldol condensation to triose intermediates that undergo subsequent isomerization and realdolization. Measured first-order glucose-sorbose isomerization rate constants (per total Ti; 373 K) for Ti-Beta in methanol were similar for unlabeled glucose and glucose deuterated at the C2 position (within a factor of ~1.1) but were a factor of ~2.3 lower for glucose deuterated at each carbon position; these H/D kinetic isotope effects were consistent with kinetically-relevant intramolecular C5-C1 hydride shift steps. Optical rotation measurements of sugar fractions isolated after the isomerization of D-(+)-glucose (92% enantiomeric purity) with Ti-Beta in water indicated that stereochemistry was preserved at carbon centers not directly involved in intramolecular C5-C1 or C2-C1 hydride shift steps that respectively form L-(−)-sorbose (73%) and D-(−)-fructose (87%) as the predominant stereoisomers. These findings describe a Lewis acid-mediated intramolecular rearrangement of glucose that, in contrast with that involved in isomerization to fructose, does not appear to have an enzymatic analog.

Example 2

Experimental Methods

Example 2.1

Catalyst Synthesis and Characterization

Procedures to synthesize Ti-Beta zeolites in fluoride media with different Si/Ti ratios were adapted from reported protocols. See Blasco, T., et al., *J. Phys. Chem. B* 1998, 102, 75-88, which is incorporated by reference herein for its teachings of syntheses. Ti-Beta samples were treated in flowing air (1.67 $cm^3$ $s^{-1}$, Air Liquide, breathing grade) at 853 K (0.0167 K $s^{-1}$) for 12 h prior to characterization and catalytic evaluation. Atomic Si and Ti contents were measured using a JEOL 8200 electron microprobe, operated in focused beam mode with a 40 micron spot size, at 15 kV and 25 nA. The Si/Ti ratio determined by electron microprobe are denoted in the suffix of sample names (e.g., Ti-Beta-79 contains a Si/Ti ratio of 79).

Figure 3:
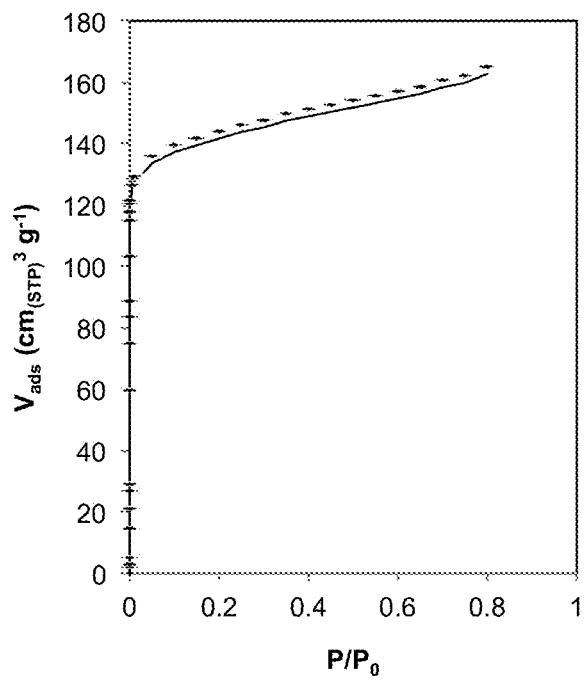
FIG. 3 shows an $N_2$ adsorption isotherm (77 K) for Ti-Beta-202 as described in Example 2.1. The adsorption branch of the $N_2$ isotherm (77 K) measured on Ti-Beta-202 is representative of that measured on all Ti-Beta samples used in the Examples provided herein. The micropore volume estimated from semilog-derivative plot analysis (details given elsewhere[4]) is 0.21 $cm^3\ g^{-1}$, which is consistent with the beta topology.
Figure 4:
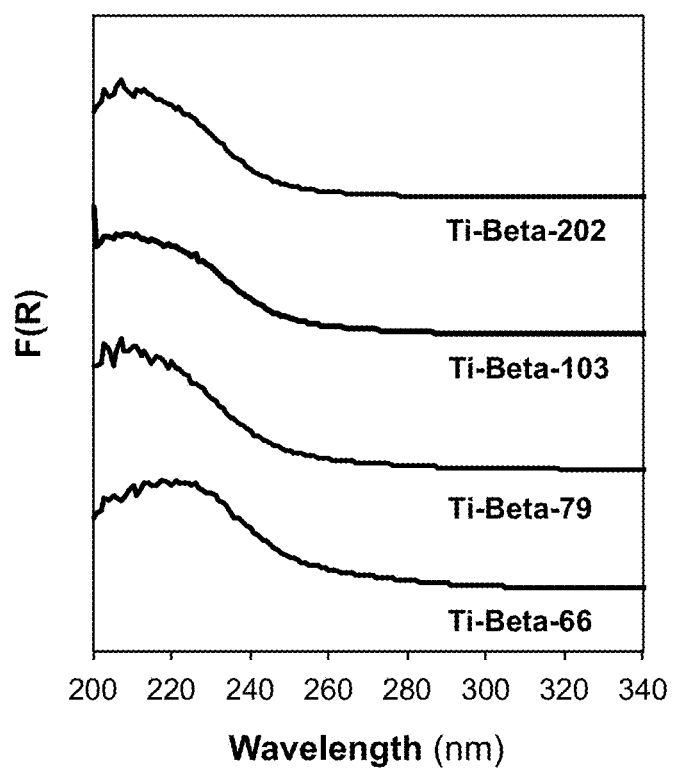
FIG. 4 shows the diffuse reflectance UV-Visible DRUV spectra of Ti-Beta-66, Ti-Beta-79, Ti-Beta-107, Ti-Beta-202 (bottom to top) as described in Example 2.1. The diffuse reflectance UV-Visible spectra in Kubelka-Munk units are shown for each Ti-Beta samples used in this study. All samples show DRUV bands centered in the 200-220 nm range, which have been assigned previously to framework $Ti^{4+}$ centers.

The crystal structures of all samples, determined from powder X-ray diffraction (XRD) patterns collected using a Rigaku Miniflex II diffractometer and Cu Kα radiation, were consistent with the beta topology (FIG. 2). $N_2$ adsorption isotherms (FIG. 3) were measured at 77 K using a Quantachrome Autosorb iQ automated gas sorption analyzer, using protocols reported elsewhere, [Gounder, R.; Davis, M. E. *AiChE J.* 2013, 59, 3349-3358] and gave micropore volumes of ~0.21 cm$^3$ g$^{-1}$ as expected from the beta topology. Diffuse reflectance UV-Visible spectra of Ti-Beta samples (FIG. 4) showed bands centered in the 200-220 nm range, which have been assigned previously to $Ti^{4+}$ centers incorporated within zeolite frameworks.

Example 2.2

Kinetic Studies of Glucose Reactions with Ti-Beta

Reactions with D-glucose (Sigma-Aldrich, ≥99%) were conducted in 10 mL thick-walled glass batch reactors (VWR), with temperature control via an oil bath located on a digital stirring hotplate (Fisher Scientific). Typical reactions with D-glucose were carried out at a 1:50 metal:glucose molar ratio and involved contacting 4 g of a 1% (w/w) glucose solution in water or in methanol with the catalytic solids in a stirred glass reactor sealed with a crimp top (PTFE/silicone septum, Agilent). Kinetic studies using isotopically-labeled glucose were performed using 1% (w/w) solutions of D-glucose-D2 (Cambridge Isotope Laboratories, ≥98%) or of D-glucose-$D_2$-1,2,3,4,5,6,6 (Cambridge Isotope Laboratories, ≥98%) in methanol.

Reactors were placed in the oil bath and small aliquots (~50-100 microliters) were extracted at various time intervals via syringe (Hamilton), filtered through a 0.2 micron PTFE filter (National Scientific), and mixed with 1% (w/w) aqueous D-mannitol (Sigma-Aldrich, ≥98%) solutions used as an internal standard for quantification. The composition of reaction aliquots was determined after separation of compounds in an Agilent 1200 high performance liquid chromatograph (HPLC) equipped with an evaporative light scattering (ELS) detector (Agilent 380 LC). Glucose, sorbose, mannose, fructose, and mannitol fractions were separated using a Hi-Plex Ca column (7.7×300 mm, 8 micron particle size, Agilent) held at 353 K, with either ultrapure water (0.010 mL s$^{-1}$ flow rate) or a 30/70 (v/v) mixture of acetonitrile/water (0.013 mL s$^{-1}$ flow rate) as the mobile phase.

Example 2.3

Isotopic and Stereochemical Characterization of Sugars

Liquid NMR analysis of products formed from isotopic tracer studies using D-glucose-D2 or D-glucose-$^{13}$C-C1 (Cambridge Isotope Laboratories, ≥98%) reactants involved separation of the glucose, sorbose, and fructose fractions by HPLC, evaporation of $H_2O$ and dissolution in $D_2O$ (Cambridge Isotope Laboratories, 99.9%). $^1H$ and $^{13}C$ liquid NMR spectra were collected on a 400 MHz NMR spectrometer (Varian) in the Caltech liquid NMR facility. Glucose, sorbose and fructose solids were subsequently isolated by evaporation of $D_2O$ and dissolved in $H_2O$ prior to measurement of optical rotation at 589 nm and ambient temperature using a Jasco P-2000 polarimeter and a 100 mm path-length cell.

Example 3

Results and Discussion

Example 3.1

Kinetic Studies of Glucose Isomerization Over Ti-Beta

Monosaccharide yields (w/w) resulting from the reaction of 1% (w/w) glucose solutions in water and in methanol over Ti-Beta samples (373 K) of varying Si/Ti content are shown in Table 1; characterization data for the samples used in this study are provided in Example 2.1.

TABLE 1

Monosaccharide Yields and Turnover Numbers from Glucose Reactions with Ti-Beta and Zr-Beta in Water and Methanol[a]

| Catalyst | Si/M ratio | Solvent | Glucose:Metal Ratio | Monosaccharide yield (w/w %) | | | | Turnover Number[b] |
|---|---|---|---|---|---|---|---|---|
| | | | | Glucose | Sorbose | Mannose | Fructose | Total |
| Ti-Beta | 66 | $H_2O$ | 32 | 82 | 4 | <0.1 | 11 | 98 | 5.0 |
| Ti-Beta | 79 | $H_2O$ | 60 | 81 | 3 | <0.1 | 8 | 93 | 6.8 |
| Ti-Beta | 107 | $H_2O$ | 56 | 80 | 4 | <0.1 | 8 | 92 | 6.4 |
| Ti-Beta | 202 | $H_2O$ | 69 | 87 | 3 | <0.1 | 6 | 96 | 5.8 |
| Zr-Beta | 182 | $H_2O$ | 78 | 90 | 1.5 | <0.1 | 6 | 97 | 5.8 |
| Ti-Beta | 66 | $CH_3OH$ | 30 | 64 | 12 | 1.1 | 8 | 85 | 6.5 |
| Ti-Beta | 79 | $CH_3OH$ | 63 | 79 | 8 | 0.7 | 4 | 92 | 8.4 |
| Ti-Beta | 107 | $CH_3OH$ | 54 | 76 | 9 | 0.8 | 4 | 90 | 7.9 |
| Ti-Beta | 202 | $CH_3OH$ | 119 | 77 | 6 | 0.6 | 4 | 88 | 13.0 |
| Zr-Beta | 182 | $CH_3OH$ | 74 | 70 | 4 | <0.5 | 22 | 95 | 18.2 |

[a]Reaction conditions: 1% (w/w) glucose solutions, 373 K, 2 h.
[b]Moles of product monosaccharides formed per moles of total Ti or Zr.

Reactions of glucose with Ti-Beta in water formed predominantly fructose together with a second previously unidentified hexose sugar, which became the predominant product of glucose reactions with Ti-Beta in methanol solvent (Table 1). This unknown hexose product was retained at times nearly identical to (within 0.2 min) that of mannose during chromatographic separation with a Ca Hi-Plex column (7.7× 300 mm, 8 micron particle size, Agilent) using water as the mobile phase (0.6 mL min$^{-1}$, 353 K). Mannose and the unknown hexose product were resolved, however, upon changing the mobile phase to a 70/30 (v/v) mixture of acetonitrile/water (0.8 mL min$^{-1}$, 353 K). $^1H$ and $^{13}C$ nuclear magnetic resonance (NMR) spectra of this previously unknown hexose product were identical to that of authentic sorbose, the C-5 epimer of fructose, as described in Que, L.; Gray, G. R. *Biochemistry* 1974, 13, 146-153.

Figure 5A:
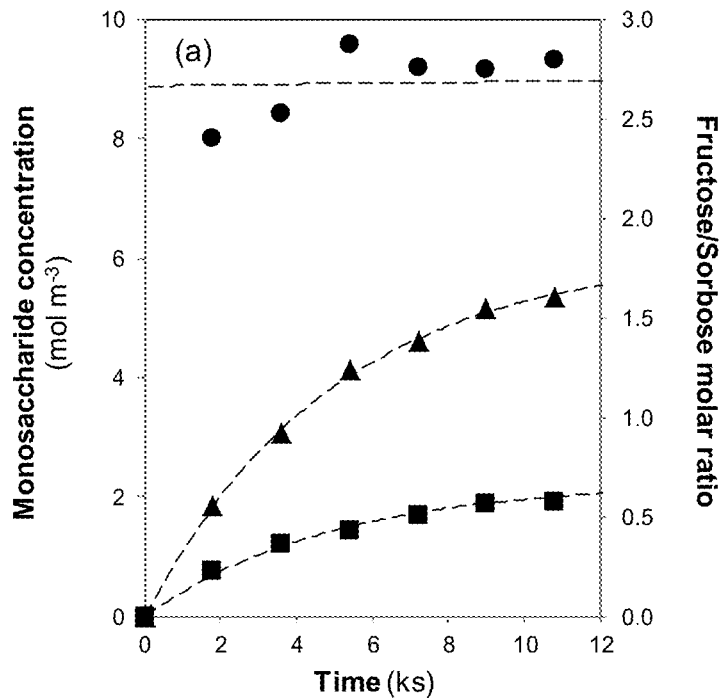
FIG. 5A-B illustrate liquid-phase concentrations of sorbose (■) and fructose (▲), and fructose-to-sorbose or sorbose-to-fructose molar ratios (●) as a function of reaction time during reaction of a 1% (w/w) solution of glucose with Ti-Beta-79 in water (FIG. 5A) and in methanol solvent (FIG. 5B). Dashed curves for liquid-phase sugar concentrations represent best fits of the experimental data to Eq. (S.1). Dashed curves for sugar molar ratios are given by the ratio of the two models for individual sugar concentrations.
Figure 5B:
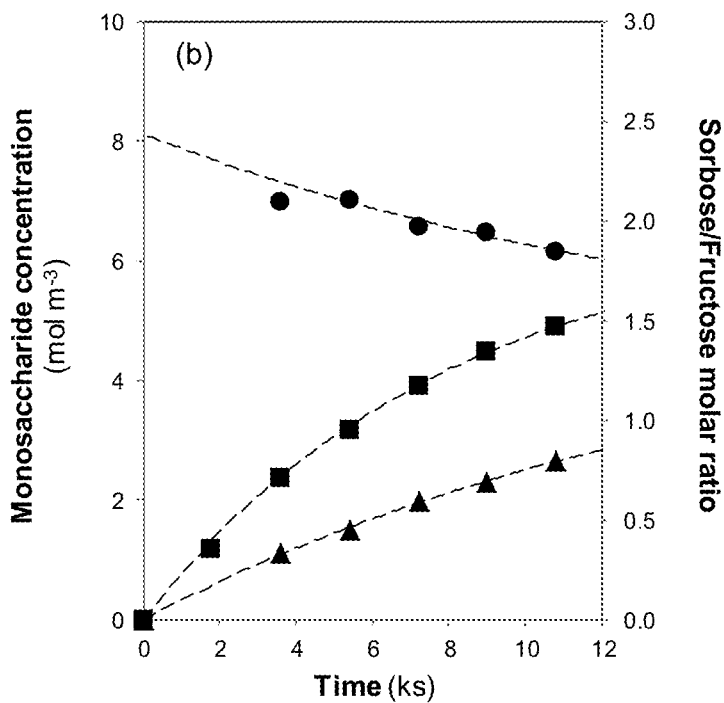

Kinetic studies of glucose reactions with Ti-Beta at 373 K, performed in batch reactors using 1% (w/w) glucose solutions in water and in methanol, showed that the evolution of liquid-phase fructose and sorbose concentrations with reaction time were described accurately by rate expressions that were first-order in glucose concentration (FIG. 5A-B). Fructose and sorbose were formed at non-zero initial turnover rates and in essentially constant molar ratios as glucose conversion increased from 0-28% (FIG. 5A-B), reflecting the formation of both products from parallel and primary reactions of glucose. This kinetic behavior is inconsistent with the formation of sorbose via 3,4-enediol intermediates formed upon sequential rearrangements of 1,2-enediols, or via sequential retro-aldol condensation of glucose to glyceraldehyde, isomerization to dihydroxyacetone, and realdolization of triose fragments as has been reported with homogeneous or heterogeneous bases. The absence of other ketohexoses (e.g., psicose, tagatose) or trioses in solution after glucose reactions with Ti-Beta (Table 1) is also inconsistent with their expected formation during base-catalyzed glucose reactions.

The evolution of liquid-phase fructose and sorbose concentrations, together with fructose-to-sorbose molar ratios, with reaction time during reaction of 1% (w/w) glucose solutions with Ti-Beta-79 in water and in methanol are shown in FIG. 5A and FIG. 5B, respectively. The dashed lines in FIG. 5A-B reflect best fits of the experimental data to kinetic models derived upon integration of fructose and sorbose formation rates in an ideal, stirred batch reactor, assuming their formation occurs in parallel, reversible reactions of glucose and at rates that are first-order in liquid phase glucose concentration:

$$c_{j(l)}(t) = c_{j(l),eq}(1 - e^{-t/\tau}) \quad (1)$$

In Eq. (1), $C_{j(l)}$ and $C_{j(l),eq}$ are liquid-phase concentrations of product j (fructose, sorbose) at time t and at equilibrium, respectively, and $\tau$ is a time constant for the approach to this equilibrium. Initial turnover rates were determined from extrapolation to zero time and provided non-zero values for rates of formation for both fructose and sorbose products, while fructose-to-sorbose molar ratios depended weakly on glucose conversion in water (0-25%) and in methanol (0-28%). Together, these data are consistent with parallel glucose-fructose and glucose-sorbose isomerization reactions in primary reaction steps.

Example 3.2

Isotopic Tracer Studies of Glucose Isomerization Over Ti-Beta

Isotopic tracer studies using glucose reactants labeled with $^{13}C$ at the C1 position (glucose-$^{13}C$-C1) or with D at the C2 position (glucose-D2), together with $^{1}H$ and $^{13}C$ NMR spectroscopic analysis of sugar products fractionated after reaction, were used to confirm the presence of Lewis acid sites on Ti-Beta and to probe the mechanism of glucose-sorbose isomerization. The $^{13}C$ NMR spectrum of unlabeled glucose is shown in FIG. 6A for reference. The glucose fraction isolated after reaction of glucose-$^{13}C$-C1 with Ti-Beta in water (373 K) showed resonances at $\delta$=95.8 and 92.0 ppm (FIG. 6B), which respectively correspond to C1 positions in $\beta$-pyranose and $\alpha$-pyranose anomers of glucose. The $^{13}C$ NMR spectrum of the glucose fraction collected after reaction of glucose-D2 with Ti-Beta in water (373 K) showed low intensity triplets present in place of sharp resonances at $\delta$=74.1 and 71.3 ppm (FIG. 6C) for the C2 positions in $\beta$-glucopyranose and $\alpha$-glucopyranose, respectively. These low intensity triplets result from the suppression of the nuclear Overhauser enhancement (NOE) of carbon resonances in $^{13}C$ NMR spectra collected using proton broad-band decoupling caused by the presence of covalently-bonded deuterium. The presence of deuterium at glucose C2 positions was also confirmed by the absence of resonances for C2-H atoms in the corresponding $^{1}H$ NMR spectrum (FIG. 7). As shown in FIG. 7A-B. The absence of resonances near $\delta$=3.1 ppm reflects the presence of a D label at the C-2 position in glucose, indicating that H/D scrambling did not occur at this position, as also observed previously on Sn-Beta. See Angyal, S. J. *Glyoscience: Epimerisation, Isomerisation and Rearrangement Reactions of Carbohydrates* 2001, 215, 1-14. These data (FIG. 6B-C) confirm that $^{13}C$ and H/D scrambling in isotopically-labeled glucose reactants does not occur during reaction or chromatographic separation.

Figure 8:
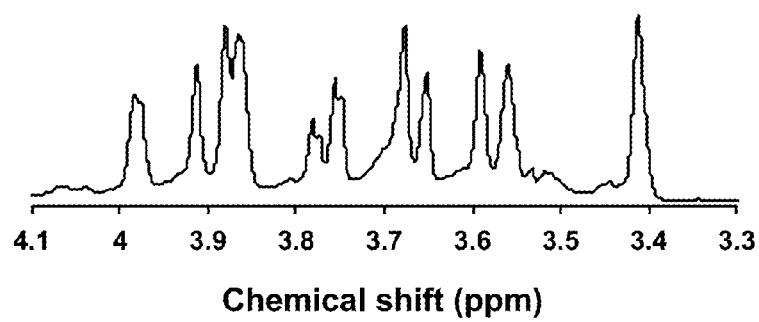
FIG. 8 is the $^{1}$H NMR spectrum of fructose fraction after reaction of glucose-D2 with Ti-Beta in water at 373 K for 6 h, described in Example 3.2.
Figure 9:
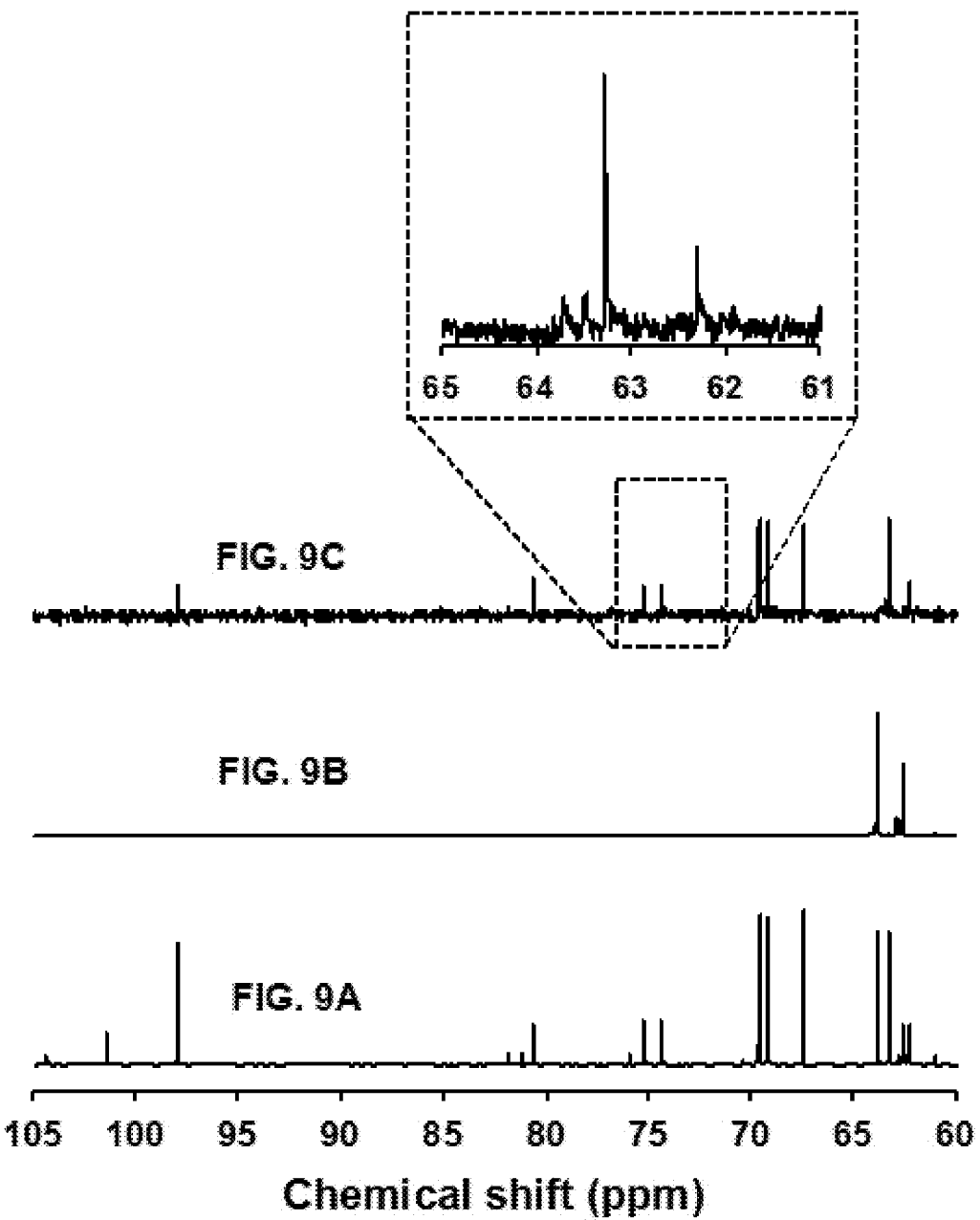
FIG. 9A-C are the $^{13}$C NMR spectra of unlabeled fructose (FIG. 9A) and of the fructose fractions isolated after reaction of glucose-$^{13}$C-C1 (FIG. 9B) and glucose-D2 (FIG. 9C) with Ti-Beta in water at 373 K for 6 h.

The fructose products formed from reaction of glucose-$^{13}C$-C1 and glucose-D2 with Ti-Beta in water contained a $^{13}C$ label at its C-1 position (fructose-$^{13}C$-C1) and a D label at its C1 position (fructose-D1) (FIG. 8 and FIG. 9), respectively, as also observed on Lewis acidic Sn-Beta. See, e.g., Roman-Leshkov, Y., et al., *Angew. Chem. Int. Ed.* 2010, 49, 8954-8957 and Bermejo-Deval, R., et al., *ACS Catal.* 2012, 2, 2705-2713.

The $^{1}H$ NMR spectrum of the fructose fraction after reaction of glucose-D2 with Ti-Beta in water is shown in FIG. 8A-B. The absence of resonances near $\delta$=3.45 ppm reflects the presence of a D label at the C-1 position in fructose, a consequence of intramolecular C2-C1 hydride shift isomerization, as also observed previously on Sn-Beta. See again, Angyal, S. J. *Glyoscience: Epimerisation, Isomerisation and Rearrangement Reactions of Carbohydrates* 2001, 215, 1-14.

The $^{13}C$ NMR spectrum of unlabeled fructose is shown in FIG. 9A for reference. The fructose fraction isolated after reaction of glucose-$^{13}C$-C1 with Ti-Beta in water (373 K) showed resonances at $\delta$=63.8 and 62.6 ppm (FIG. 9B), which correspond to C1 positions in $\beta$-pyranose and $\beta$-furanose anomers of fructose, respectively. The $^{13}C$ NMR spectrum of the fructose fraction collected after reaction of glucose-D2 with Ti-Beta in water (373 K) showed low intensity triplets present in place of sharp resonances at $\delta$=63.8 and 62.6 ppm (FIG. 9C) for the C1 positions in $\gamma$-fructopyranose and $\beta$-fructofuranose, respectively, reflecting the presence deuterium atoms bound to C1 centers. These data are consistent with the $^{1}H$ NMR spectrum shown in FIG. 8 and confirm the presence of Lewis acidic framework $Ti^{4+}$ centers in Ti-Beta.

These isotopic tracer studies confirm that glucose-fructose isomerization occurs via an intramolecular hydride shift from the C2 to C1 position, with undetectable contributions from minority base sites that would have otherwise mediated reversible enolization to cause H/D scrambling at the C2 position of glucose and, in turn, fructose products formed without D atoms retained at their C1 position. From these data, it appears that the Lewis acidic framework $Ti^{4+}$ sites in Ti-Beta are solely responsible for mediating glucose isomerization routes.

Figure 10:
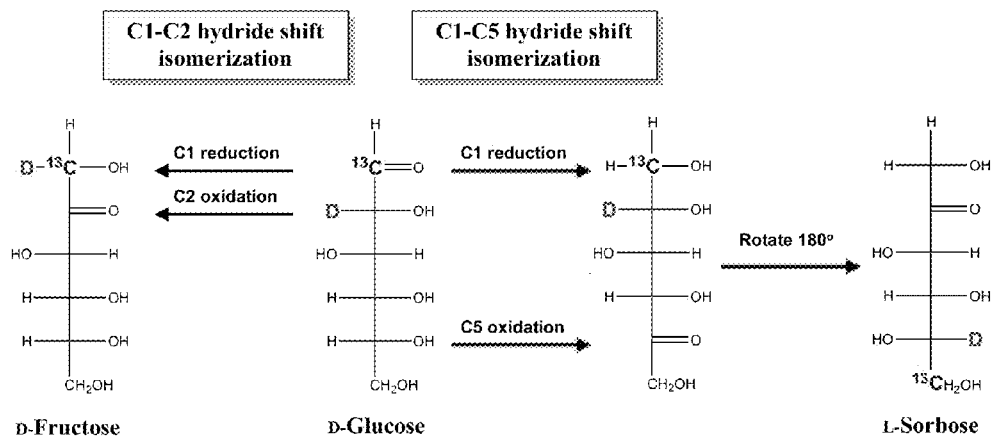
FIG. 10 illustrates the parallel reaction schemes for glucose-fructose and glucose-sorbose isomerization mediated by Lewis acidic $Ti^{4+}$ centers in Ti-Beta. Mechanistic evidence from isotopic tracer studies using D and $^{13}$C labels shown in reactants and products depicted using Fischer projections.

The $^{13}C$ NMR spectrum of unlabeled sorbose is provided in FIG. 6D, together with positional assignments for each carbon atom in a-L-sorbopyranose. The $^{13}C$ NMR spectrum of the sorbose fraction isolated after reaction of glucose-$^{13}C$-C1 with Ti-Beta in water showed a single resonance at $\delta$=61.7 ppm (FIG. 6E), which corresponds to the C-6 position. In contrast, base-mediated glucose-$^{14}C$-C1 isomerization via symmetric 3,4-enediol intermediates would form sorbose with $^{14}$C labels at both the C1 and C6 positions, while isomerization via sequential retro-aldol condensation, isomerization and realdolization reactions would lead to $^{14}$C label redistribution throughout the sorbose backbone. See, e.g., Elkhadem, H. S. et al., *Carbohydrate Research* 1987, 169, 13-21 and Sowden, J. C, et al., *J. Am. Chem. Soc.* 1958, 80, 1435-1438. The $^{13}$C NMR spectrum of sorbose formed form reaction of glucose-D2 with Ti-Beta showed resonances for all carbon atoms except that for the C5 position at δ=70.3 ppm (FIG. 6F), whose NOE is suppressed by D atoms bound to C5 centers. In contrast, base-mediated glucose isomerization initiated via a-carbonyl proton abstraction would have caused H/D scrambling at C2 positions of glucose and the incorporation of H atoms at C5 positions of sorbose. Thus, $^{13}$C and D atoms at glucose C1 and C2 locations are respectively retained at C6 and C5 locations in sorbose upon isomerization (FIG. 10). The atomic redistributions involved in isomerization of glucose to sorbose, which occur between opposite ends of ring-opened hexose chains, at first glance appear to require several skeletal rearrangement steps. Yet, in fact, they would only require glucose C1 aldehyde-to-alcohol reduction and C5 alcohol-to-ketone oxidation (FIG. 10) either in a concerted or in sequential steps.

Example 3.3

Proposed Mechanism for Glucose-Sorbose Isomerization on Ti-Beta

While not intending to be bound by the correctness of any particular theory, it is possible that the glucose-sorbose isomerization occurs via a concerted intramolecular MPVO step mediated by an intramolecular hydride shift from the C5 to the C1 position on open glucose chains (FIG. 11), in an analogous intramolecular MPVO mechanism for glucose-fructose isomerization mediated by C2-C1 intramolecular hydride shift. Quantum chemical studies of glucose-fructose isomerization on Sn-Beta and Ti-Beta open sites (three framework —OSi bonds and one —OH group) have shown that coordination of oxygen atoms in C1-O—O5 ether linkages of cyclic glucose at Lewis acidic framework metal (M=Sn, Ti) sites (1, FIG. 11) and subsequent metal-mediated ring-opening (2, FIG. 11) results in open-chain glucose bound to metal centers via O1 and O5 atoms (3, FIG. 11). Theoretical studies indicate that intramolecular C2-C1 hydride shifts in glucose-fructose isomerization, in fact, requires proton-transfer from M-(OH2) groups to glucose O5 atoms in intermediate 3 (FIG. 11) to form C5-OH groups, desorption of C5-OH groups from M sites, adsorption of C2-OH moieties after rotation of glucose bound solely via O1 atoms, and deprotonation of C2-OH groups by M-OH moieties to enable bidentate coordination of O1 and O2 atoms. See, e.g., Bermejo-Deval, R., et al., *Proc. Nall. Acad. Sci. USA* 2012, 109, 9727-9732. Glucose-sorbose isomerization instead would only require an alternate reaction sequence beginning with intermediate 3 (FIG. 11), involving intramolecular C5-C1 hydride shift (4, FIG. 11) to form open-chain sorbose bound via O2 and O6 atoms (5, FIG. 11), followed by protonation of sorbose O6 atoms to C6-OH groups (6, FIG. 11) and sorbose ring-closing (7, FIG. 11). In this proposal, the reaction coordinates for glucose-fructose and glucose-sorbose isomerization share common elementary steps for binding and ring-opening of cyclic glucose at framework metal centers (Steps a and b, FIG. 11). These mechanistic features are consistent with the sole formation of fructose and sorbose with Lewis acidic Ti-Beta (Table 1) and the absence of psicose and tagatose isomers, which are formed concomitantly with fructose and sorbose via interconvertible enediol intermediates on homogeneous or heterogeneous base catalysts.

Figure 12A:
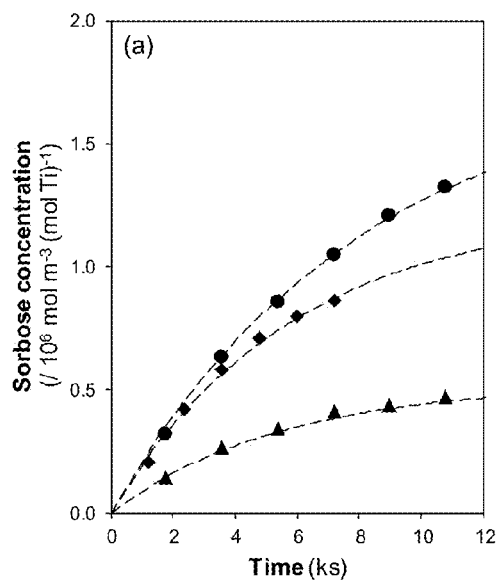
FIG. 12A-B illustrate the liquid-phase concentrations of sorbose (FIG. 12A) and fructose (FIG. 12B) as a function of reaction time during reaction of a 1% (w/w) solution of glucose (●), glucose-D2 (♦), or glucose-$D_7$-1,2,3,4,5,6,6 (▲) with Ti-Beta in methanol solvent (373 K). Corresponding initial turnover rates are given in Table 2. Dashed curves represent best fits of the experimental data to kinetic models derived assuming isomerization to sorbose and fructose occur in parallel and at rates that are first-order in glucose concentration.
Figure 12B:
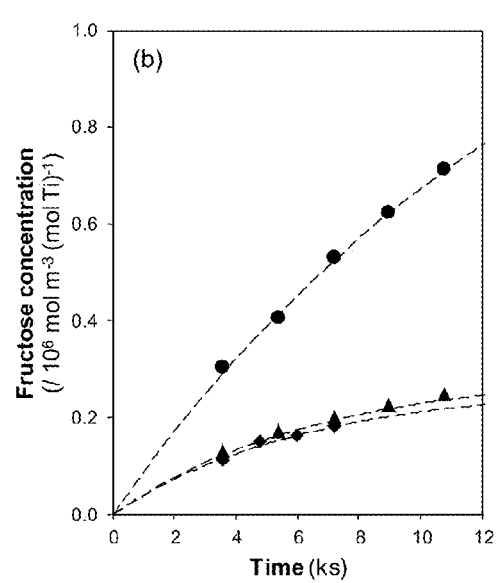
Figure 13:
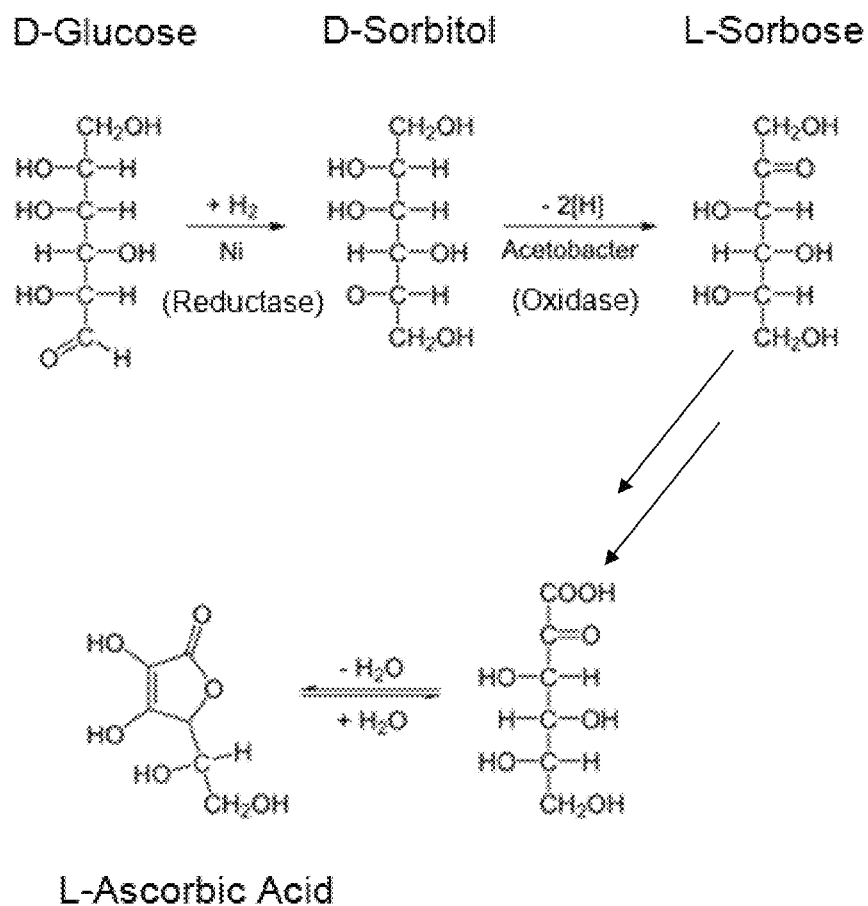
FIG. 13 illustrates a scheme of the reactions associated with the Reichstein process for the production of vitamin C (ascorbic acid).

Initial turnover rates (per total Ti; 373 K) for glucose isomerization to sorbose and isomerization to fructose with Ti-Beta in methanol were determined from the evolution of sorbose (FIG. 12A) and fructose (FIG. 12B) concentrations with reaction time (see Example 3.1, above). Measured first-order isomerization rate constants derived from these initial turnover rates (FIG. 12A and FIG. 12B) when glucose with different locations and amounts of isotopic deuterium labels were used as reactants are shown in Table 2.

TABLE 2

Measured First-Order Rate Constants and H/D Kinetic Isotope Effects (373 K) for Glucose Isomerization to Sorbose and Isomerization to Fructose in Methanol[a]

| Reactant | Measured rate constant (373 K) ($/10^{-6}$ mol (mol Ti*s*((mol glucose)*$m^{-3}$))$^{-1}$) | | Kinetic isotope effect (KIE)[b] | |
|---|---|---|---|---|
| | Sorbose | Fructose | Sorbose | Fructose |
| Glucose | 27 ± 1.3 | 11 ± 0.6 | | |
| Glucose-D2 | 25 ± 1.2 | 5.0 ± 0.2 | 1.1 ± 0.1 | 2.2 ± 0.3 |
| Glucose-D$_7$-1,2,3,4,5,6,6 | 12 ± 0.6 | 5.4 ± 0.3 | 2.3 ± 0.2 | 2.0 ± 0.2 |

[a]Calculated from turnover rates measured on Ti-Beta-79 (shown in FIG. 12).
[b]Given by the ratio of the rate constant for non-deuterated glucose relative to that for deuterated reactants.

Rate constants for glucose-fructose isomerization (per total Ti; 373 K) were higher by a factor of ~2.2 for unlabeled glucose than for glucose-D2 (Table 2) on Ti-Beta in methanol, consistent with glucose-fructose isomerization via a kinetically-relevant intramolecular C2-C1 hydride shift (See Example 3.4, below), as also observed on Sn-Beta and Ti-Beta in water in other studies. Initial turnover rates for glucose-sorbose isomerization were essentially identical (within a factor of ~1.1) for glucose and glucose-D2 reactants in methanol, indicating that C2-D bonds remain intact during such isomerizations. The reaction of fully-deuterated glucose (glucose-D$_7$-1,2,3,4,5,6,6) led to an observed KIE for glucose-fructose isomerization of ~2.0 in methanol solvent (Table 2), because C2-D bonds are broken in kinetically-relevant steps, and also led to a similar KIE of ~2.3 for glucose-sorbose isomerization (Table 2). The KIE values of ~1.1 and ~2.3 for glucose-sorbose isomerization when glucose reactants are deuterated at the C-2 position and at all positions, respectively, reflect the kinetic relevance of C-D bond breaking steps at a position other than C-2. Although we are unable to probe C5-D cleavage directly because glucose-D5 reactants are unavailable, the KIE of ~2.3 observed with fully deuterated glucose reactants is expected from kinetically-relevant C5-D bond cleavage (See Example 3.4, below), as required for the proposed intramolecular C5-C1 hydride shift mechanism (FIG. 11) and consistent with the isotopic tracer studies (FIG. 10) that led to this proposal.

Example 3.4

Estimation of the Kinetic Isotope Effect for Intramolecular H-Shift Isomerization The H/D kinetic isotope effect (KIE) for glucose-fructose isomerization via intramolecular C2-C1 hydride shift at 373 K was estimated from the following expression derived using transition state theory:

$$\frac{k_H}{k_D} = e^{\left(\frac{ZPE_H - ZPE_D}{kT}\right)} = e^{\left(\frac{0.13 hc\overline{v_H}}{kT}\right)} \quad (S.2)$$

in which $$ZPE = \frac{1}{2}hc\overline{v} \quad (S.3)$$

$$\frac{\overline{v_H}}{\overline{v_D}} \cong 0.74 \quad (S.4)$$

where h is Planck's constant ($6.63 \times 10^{-34}$ m$^2$ kg s$^{-1}$), c is the speed of light ($2.998 \times 10^8$ m s$^{-1}$), k is Boltzmann's constant ($1.38 \times 10^{-23}$ m$^2$ kg s$^{-2}$ K$^{-1}$), T is the temperature (373 K) and $\overline{v_H}$ is the vibrational frequency of a C—H bond scissoring vibration (150000 m$^{-1}$).

Substitution of these values into Eq. (S.2) gives a value of ~2.1, which is the H/D KIE expected if measured rates were limited by the hydride shift isomerization rates. If reaction rates were limited by intraparticle mass transfer, measured rate constants are proportional to the square root of the reaction rate constant, and the observed H/D KIE is given by:

$$\left(\frac{k_H}{k_D}\right)_{obs} = \left(\frac{k_H}{k_D}\right)^{0.5} \quad (S.5)$$

or a value of ~1.5.

The assumption that intramolecular C5-C1 hydride shifts that mediate glucose-sorbose isomerization also involve a C—H bond scissoring vibration (~150000 m$^{-1}$) would lead to an equivalent H/D isotope effect of ~2.1 for glucose deuterated at the C5 carbon.

Example 3.5

Stereochemical Isomerization Mediated by Lewis Acid Sites

The proposed glucose-sorbose isomerization mechanism involves the reduction of C1 centers and the oxidation of C5 centers in D-glucose, but does not change the oxidation states or stereochemistry of C2, C3 and C4 centers (FIG. 10). Thus, D-glucose isomerization via C5-C1 hydride shift should selectively form L-sorbose, while isomerization via C2-C1 hydride shift should, by a similar argument, selectively form D-fructose. The glucose, sorbose and fructose fractions isolated after reaction of a 10% (w/w) aqueous solution of glucose-D2 with Ti-Beta (373 K, 6 h), and after collection of $^1$H and $^{13}$C NMR spectra (FIGS. 6 to 9) and replacement of D$_2$O with H$_2$O as the solvent, were tested for optical activity at ambient temperature at 589 nm. The specific optical rotations of the glucose, sorbose and fructose fractions were 44.7±0.1°, −19.8±0.6° and −67.6±2.7°, respectively (Table 3), reflecting the presence of predominantly D-(+)-glucose, L-(−)-sorbose and D-(−)-fructose stereoisomers within the respective fractions.

TABLE 3

Specific Rotation and Enantiomeric Compositions of Glucose, Sorbose and Fructose Fractions Isolated After Reaction of Glucose-D2 with Ti-Beta in Water[a]

| Fraction | Specific rotation[b] (°) | Enantiomeric Excess[c] (%) | D-enantiomer (%) | L-enantiomer (%) |
|---|---|---|---|---|
| Glucose | 44.7 ± 0.1 | 85 ± 0.3 | 92 ± 1 | 8 ± 1 |
| Sorbose | −19.8 ± 0.6 | 46 ± 1.5 | 27 ± 1 | 73 ± 1 |
| Fructose | −67.6 ± 2.7 | 73 ± 3 | 87 ± 2 | 13 ± 2 |

[a]Reaction conditions: 10% (w/w) aqueous glucose-D2 solution, Ti-Beta-79, 373 K, 6 h.
[b]Optical rotations measured at 589 nm at ambient temperature.
[c]Calculated assuming each sugar fraction contained only a mixture of the two enantiomers, using the following enantiomer optical rotation values: D-(+)-glucose: 52.7°, L-(−)-sorbose: −42.7°, D-(−)-fructose: −92.4°.

Table 3 also shows estimated values for the enantiomeric excess and composition of each fraction, indicating that isomerization reactions of D-(+)-glucose-D2 (92% enantiomeric purity) with Ti-Beta selectively formed L-(−)-sorbose-D5 (73%) and D-(−)-fructose-D1 (87%).

Figure 11A:
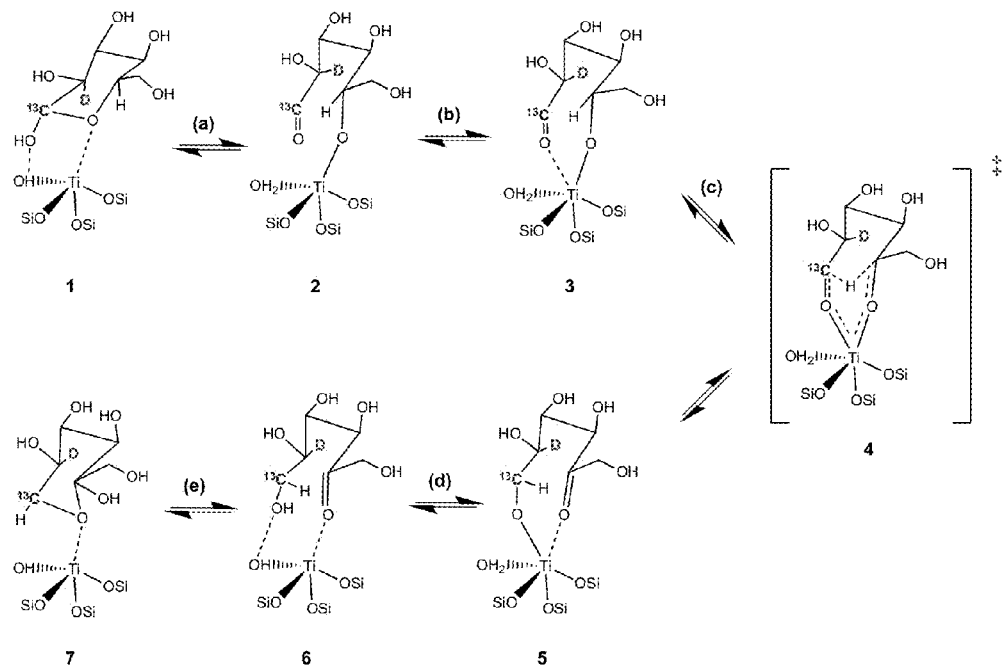
FIG. 11A illustrates a possible intermediate (1-3, 5-7) and transition state (4) structures involved in the proposed intramolecular C5-C1 hydride shift reaction mechanism for glucose-sorbose isomerization on open sites in Ti-Beta.
Figure 11B:
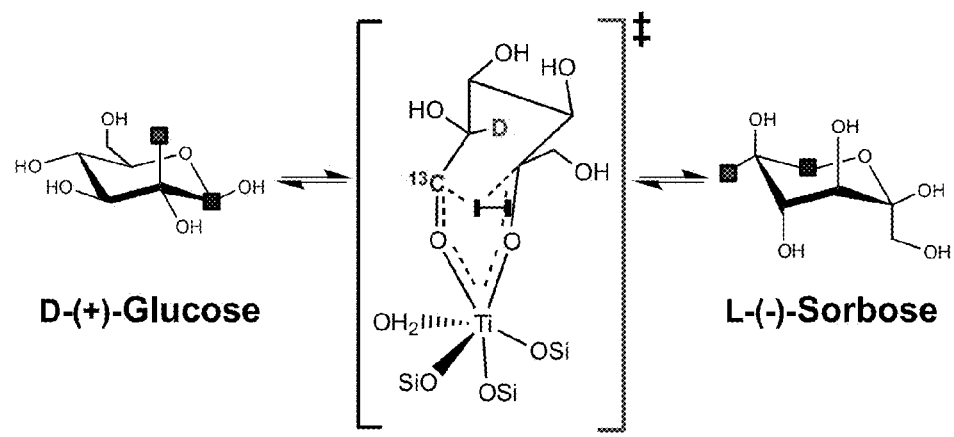
FIG. 11B provides an overview of the reaction of glucose to sorbose using this intermediate state (4).

The predominant formation of L-(−)-sorbose and D-(−)-fructose from reactions of D-(+)-glucose with Ti-Beta is consistent with intramolecular hydride shift isomerizations mediated by Lewis acidic Ti centers, and specifically with the intramolecular C5-C1 hydride shift proposed for glucose-sorbose isomerization (FIG. 11). Such stereochemical specificity is in sharp contrast to that expected from base-catalyzed D-glucose isomerization via 3,4-enediol intermediates, which leads to the predominant formation of D-(+)-sorbose (68%) over L-(−)-sorbose (32%).[27] Such stereospecificity also contrasts sharply that expected from base-mediated retro aldol condensation to L-glyceraldehyde and realdolization with dihydroxyacetone, which would form similar amounts of L-(−)-sorbose and L-(+)-fructose.

Direct glucose-fructose isomerization via intramolecular C2-C1 hydride shifts mediated by Ti-Beta has known metalloenzyme analogs (e.g., D-xylose isomerase),[11-12] in which two divalent cations in enzyme active site pockets must interact in a concerted manner with glucose O1 and O2 atoms prior to isomerization. In contrast, direct glucose-sorbose isomerization via intramolecular C5-C1 hydride shifts mediated by Ti-Beta does not appear to have a known enzymatic analog. As a result, currently known routes for D-glucose to L-sorbose isomerization appear to require sequential reduction to a sugar alcohol and oxidation to sorbose, mediated either by a metal-enzyme or an enzyme-enzyme pair. This observation suggests that enzymatic active sites that selectively bind glucose via O1 and O5 atoms may not be as prevalent as those that bind glucose via O1 and O2 atoms, in part, resulting in the scarcity of L-sorbose found in nature, relative to the seven most abundant hexose and pentose sugars. These findings indicate that Lewis acidic metal centers in synthetic molecular sieve frameworks that can coordinate selectively with two oxygenated moieties along sugar backbones may be able to facilitate direct and stereospecific sugar rearrangements that occur rarely in biological systems.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A process for preparing sorbose from glucose, said process comprising:
   (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose; and
   (b) separating the sorbose from the starting materials and co-products.

2. A process for preparing ascorbic acid, said process comprising:
   (a) contacting the glucose with a silica-containing structure comprising a zeolite having a topology of a 12 membered-ring or larger, an ordered mesoporous silica material, or an amorphous silica, said structure containing Lewis acidic $Ti^{4+}$ or $Zr^{4+}$ or both $Ti^{4+}$ and $Zr^{4+}$ framework centers, said contacting conducted under reaction conditions sufficient to isomerize the glucose to sorbose;
   (b) optionally separating the sorbose; and
   (c) converting the sorbose to ascorbic acid.

3. The process of claim 2, wherein the process comprises:
   (a) contacting the glucose with the silica zeolite containing the Lewis acidic $Ti^{4+}$ or $Zr^{4+}$ or both $Ti^{4+}$ and $Zr^{4+}$ framework centers under reaction conditions sufficient to isomerize the glucose to sorbose.

4. The process of claim 2, wherein the silica zeolite comprises a Ti-Beta zeolite.

5. The process of claim 2, wherein the process comprises:
   (a) contacting the glucose with the ordered mesoporous silica material containing Lewis acidic $Ti^{4+}$ or $Zr^{4+}$ or both $Ti^{4+}$ and $Zr^{4+}$ framework centers under reaction conditions sufficient to isomerize the glucose to sorbose.

6. The process of claim 2, wherein the process comprises:
   (a) contacting the glucose with the amorphous silica containing Lewis acidic $Ti^{4+}$ or $Zr^{4+}$ or both $Ti^{4+}$ and $Zr^{4+}$ framework centers under reaction conditions sufficient to isomerize the glucose to sorbose.

7. The process of claim 2, wherein the silica-containing structure contains Lewis acidic $Ti^{4+}$ framework centers.

8. The process of claim 2, wherein the sorbose is L-(−)-sorbose and the glucose is D-(+)-glucose.

9. The process of claim 2, wherein the ascorbic acid is L-ascorbic acid.

10. The process of claim 2, wherein the reaction conditions comprise contacting the glucose with the silica zeolite, ordered mesoporous silica material, or amorphous silica containing the Lewis acidic $Ti^{4+}$ or $Zr^{4+}$ or both $Ti^{4+}$ and $Zr^{4+}$ framework in the presence of an aqueous or an alcoholic medium.

11. The process of claim 2, wherein the reaction conditions comprise contacting the glucose with the zeolite in the presence of an alcohol.

12. The process of claim 10, wherein the alcohol is methanol.

13. The process of claim 2, wherein the zeolite has a composition such that the atomic ratio of Si to Ti, Zr, or combination of Ti and Zr is in a range of from about 35 to about 250.

14. The process of claim 13, wherein the zeolite has a composition such that the atomic ratio of Si to Ti, Zr, or combination of Ti and Zr is in a range of from about 65 to about 120.

15. The process of claim 2, wherein the molar ratio of glucose to Ti, Zr, or combination of Ti and Zr, is in a range is in a range of from about 5 to about 500.

16. The process of claim 2, wherein the glucose is present in an aqueous solvent and the glucose concentration in the aqueous solvent is in a range of from about 0.1 w/w to about 45 w/w, relative to the weight of the solvent.

17. The process of claim 2, wherein the glucose is present in a methanolic solvent and the glucose concentration in the methanol solvent is in a range of from about 0.1 w/w to about 2 w/w, relative to the weight of the solvent.

18. The process of claim 2, wherein the reaction conditions comprise heating the reaction mixture to a temperature in a range of from about 60° C. to about 200° C.

19. The process of claim 2, wherein the sorbose is separated or isolated by filtration, crystallization, freeze-thawing, chromatographic separation, solvent removal, or a combination thereof.

20. The process of claim 2, wherein converting the sorbose to ascorbic acid comprises a sequential oxidation step followed by a step of gamma lactonization with removal of water.

21. The process of claim 18, wherein the reaction conditions comprise heating the reaction mixture to a temperature in a range of from about 80° C. to about 120° C.

22. The process of claim 1, wherein the process comprises:
   (a) contacting the glucose with the silica zeolite containing the Lewis acidic $Ti^{4+}$ or $Zr^{4+}$ or both $Ti^{4+}$ and $Zr^{4+}$ framework centers under reaction conditions sufficient to isomerize the glucose to sorbose.

23. The process of claim 1, wherein the silica zeolite comprises a Ti-Beta zeolite.

24. The process of claim 1, wherein the process comprises:
   (a) contacting the glucose with the ordered mesoporous silica material containing Lewis acidic $Ti^{4+}$ or $Zr^{4+}$ or both $Ti^{4+}$ and $Zr^{4+}$ framework centers under reaction conditions sufficient to isomerize the glucose to sorbose.

25. The process of claim 1, wherein the process comprises:
   (a) contacting the glucose with the amorphous silica containing Lewis acidic $Ti^{4+}$ or $Zr^{4+}$ or both $Ti^{4+}$ and $Zr^{4+}$ framework centers under reaction conditions sufficient to isomerize the glucose to sorbose.

26. The process of claim 1, wherein the silica-containing structure contains Lewis acidic $Ti^{4+}$ framework centers.

27. The process of claim 1, wherein the sorbose is L-(−)-sorbose and the glucose is D-(+)-glucose.

28. The process of claim 1, wherein the reaction conditions comprise contacting the glucose with the silica zeolite, ordered mesoporous silica material, or amorphous silica containing the Lewis acidic $Ti^{4+}$ or $Zr^{4+}$ or both $Ti^{4+}$ and $Zr^{4+}$ framework in the presence of an aqueous or an alcoholic medium.

29. The process of claim 1, wherein the reaction conditions comprise contacting the glucose with the zeolite in the presence of an alcohol.

30. The process of claim 29, wherein the alcohol is methanol.

31. The process of claim 1, wherein the zeolite has a composition such that the atomic ratio of Si to Ti, Zr, or combination of Ti and Zr is in a range of from about 35 to about 250.

32. The process of claim 31, wherein the zeolite has a composition such that the atomic ratio of Si to Ti, Zr, or combination of Ti and Zr is in a range of from about 65 to about 120.

33. The process of claim 1, wherein the molar ratio of glucose to Ti, Zr, or combination of Ti and Zr, is in a range is in a range of from about 5 to about 500.

34. The process of claim 1, wherein the glucose is present in an aqueous solvent and the glucose concentration in the aqueous solvent is in a range of from about 0.1 w/w to about 45 w/w, relative to the weight of the solvent.

35. The process of claim 1, wherein the glucose is present in a methanolic solvent and the glucose concentration in the methanol solvent is in a range of from about 0.1 w/w to about 2 w/w, relative to the weight of the solvent.

36. The process of claim 1, wherein the reaction conditions comprise heating the reaction mixture to a temperature in a range of from about 60° C. to about 200° C.

37. The process of claim 36, wherein the reaction conditions comprise heating the reaction mixture to a temperature in a range of from about 80° C. to about 120° C.

38. The process of claim 1, wherein the sorbose is separated or isolated by filtration, crystallization, freeze-thawing, chromatographic separation, solvent removal, or a combination thereof.

39. The process of claim 2, comprising forming 2-keto-L-gulonic acid by (a) acetal protection of ring hydroxyls of the sorbose followed by the chemical oxidation of the protected sorbose by hypochlorite or permanganate; or (b) oxidation of the sorbose using oxygen and a noble metal catalyst, such as platinum; or both (a) and (b).

40. The process of claim 39, further comprising employing conditions to ring close by gamma-lactonization of the 2-keto-L-gulonic acid, with removal of water.

* * * * *